United States Patent
Nikolchev

(10) Patent No.: US 8,016,869 B2
(45) Date of Patent: Sep. 13, 2011

(54) GUIDEWIRE-LESS STENT DELIVERY METHODS

(75) Inventor: Julian Nikolchev, Portola Valley, CA (US)

(73) Assignee: Biosensors International Group, Ltd., Hamilton (BM)

( * ) Notice: Subject to any disclaimer, the term of this patent is extended or adjusted under 35 U.S.C. 154(b) by 952 days.

(21) Appl. No.: 10/745,778

(22) Filed: Dec. 24, 2003

(65) Prior Publication Data

US 2004/0220585 A1    Nov. 4, 2004

Related U.S. Application Data

(60) Provisional application No. 60/458,323, filed on Mar. 26, 2003, provisional application No. 60/462,219, filed on Apr. 10, 2003.

(51) Int. Cl.
*A61F 2/06* (2006.01)
(52) U.S. Cl. ...................................... 623/1.11
(58) Field of Classification Search .............. 623/1.11, 623/1.13; 606/108, 200
See application file for complete search history.

(56) References Cited

U.S. PATENT DOCUMENTS

| | | | |
|---|---|---|---|
| 4,503,569 A | 3/1985 | Dotter |
| 4,512,338 A | 4/1985 | Balko et al. |
| 4,553,545 A | 11/1985 | Maass et al. |
| 4,562,596 A | 1/1986 | Kornberg |
| 4,580,568 A | 4/1986 | Gianturco |
| 4,655,771 A | 4/1987 | Wallsten |
| 4,665,918 A | 5/1987 | Garza et al. |
| 4,732,152 A | 3/1988 | Wallsten et al. |
| 4,733,665 A | 3/1988 | Palmaz |
| 4,762,128 A | 8/1988 | Rosenbluth |
| 4,768,507 A | 9/1988 | Fischell et al. |
| 4,771,773 A | 9/1988 | Kropf |
| 4,776,337 A | 10/1988 | Palmaz |
| 4,830,003 A | 5/1989 | Wolff et al. |
| 4,848,343 A | 7/1989 | Wallsten et al. |
| 4,875,480 A | 10/1989 | Imbert |
| 4,878,906 A | 11/1989 | Lindemann et al. |
| 4,893,623 A | 1/1990 | Rosenbluth |
| 4,913,141 A | 4/1990 | Hillstead |
| 4,950,227 A | 8/1990 | Savin et al. |

(Continued)

FOREIGN PATENT DOCUMENTS

DE    4420142    12/1995

(Continued)

OTHER PUBLICATIONS

Schuessler et al., Stent Materials and Manufacturing: Requirements and Possibilities/Opportunities, ASM Materials & Processes, Anaheim, CA. (Sep. 8-10, 2003).

(Continued)

*Primary Examiner* — Gary Jackson
*Assistant Examiner* — Erin Colello
(74) *Attorney, Agent, or Firm* — Kilpatrick Townsend & Stockton LLP

(57) ABSTRACT

The invention provides an atraumatic, low profile device for the delivery of one or more implants into tubular organs or open regions of the body. The implant delivery device may simultaneously or independently release portions of the implant, e.g., the proximal and distal ends of the implant. This independent release feature allows better implant positioning at the target site. Upon deployment, the implants may be placed at the target site without a sheath.

13 Claims, 13 Drawing Sheets

U.S. PATENT DOCUMENTS

| | | | |
|---|---|---|---|
| 4,954,126 A | 9/1990 | Wallsten | |
| 4,969,890 A | 11/1990 | Sugita et al. | |
| 4,990,151 A | 2/1991 | Wallsten | |
| 4,990,155 A | 2/1991 | Wilkoff | |
| 4,998,539 A | 3/1991 | Delsanti | |
| 5,019,085 A | 5/1991 | Hillstead | |
| 5,019,090 A | 5/1991 | Pinchuk | |
| 5,026,377 A | 6/1991 | Burton et al. | |
| 5,035,706 A | 7/1991 | Giantureo et al. | |
| 5,061,275 A | 10/1991 | Wallsten et al. | |
| 5,064,435 A | 11/1991 | Porter | |
| 5,067,957 A | 11/1991 | Jervis | |
| 5,071,407 A | 12/1991 | Termin et al. | |
| 5,089,006 A | 2/1992 | Stiles | |
| 5,092,877 A | 3/1992 | Pinchuk | |
| 5,102,417 A | 4/1992 | Palmaz | |
| 5,108,407 A | 4/1992 | Geremia et al. | |
| 5,108,416 A | 4/1992 | Ryan et al. | |
| 5,122,136 A | 6/1992 | Guglielmi et al. | |
| 5,147,370 A | 9/1992 | McNamara et al. | |
| 5,158,548 A | 10/1992 | Lau et al. | |
| 5,160,341 A | 11/1992 | Brenneman et al. | |
| 5,180,367 A * | 1/1993 | Kontos et al. | 604/101.04 |
| 5,192,297 A | 3/1993 | Hull | |
| 5,201,757 A * | 4/1993 | Heyn et al. | 606/198 |
| 5,221,261 A | 6/1993 | Termin et al. | |
| 5,242,399 A | 9/1993 | Lau et al. | |
| 5,242,452 A | 9/1993 | Inoue | |
| 5,246,445 A | 9/1993 | Yachia et al. | |
| 5,263,964 A | 11/1993 | Purdy | |
| 5,266,073 A | 11/1993 | Wall | |
| 5,290,305 A | 3/1994 | Inoue | |
| 5,306,294 A | 4/1994 | Winston et al. | |
| 5,320,635 A | 6/1994 | Smith | |
| 5,334,210 A | 8/1994 | Gianturco | |
| 5,354,295 A | 10/1994 | Guglielmi et al. | |
| 5,360,401 A | 11/1994 | Turnland et al. | |
| 5,372,600 A | 12/1994 | Beyar et al. | |
| 5,382,259 A | 1/1995 | Phelps et al. | |
| 5,405,378 A | 4/1995 | Strecker | |
| 5,407,432 A * | 4/1995 | Solar | 604/164.01 |
| 5,415,664 A | 5/1995 | Pinchuk | |
| 5,423,829 A | 6/1995 | Pham et al. | |
| 5,433,723 A | 7/1995 | Lindenberg et al. | |
| 5,443,477 A | 8/1995 | Marin et al. | |
| 5,445,646 A | 8/1995 | Euteneuer et al. | |
| 5,476,505 A | 12/1995 | Limon | |
| 5,484,444 A | 1/1996 | Braunschweiler et al. | |
| 5,486,195 A * | 1/1996 | Myers et al. | 606/213 |
| 5,507,771 A | 4/1996 | Gianturco | |
| 5,522,836 A | 6/1996 | Palermo | |
| 5,522,883 A | 6/1996 | Slater et al. | |
| 5,534,007 A | 7/1996 | St. Germain et al. | |
| 5,540,680 A | 7/1996 | Guglielmi et al. | |
| 5,554,181 A | 9/1996 | Das | |
| 5,569,245 A | 10/1996 | Guglielmi et al. | |
| 5,571,135 A | 11/1996 | Fraser et al. | |
| 5,578,074 A | 11/1996 | Mirigian | |
| 5,591,196 A | 1/1997 | Marin et al. | |
| 5,601,600 A | 2/1997 | Ton | |
| 5,618,300 A | 4/1997 | Marin et al. | |
| 5,634,928 A | 6/1997 | Fischell et al. | |
| 5,639,274 A | 6/1997 | Fischell et al. | |
| 5,643,254 A | 7/1997 | Scheldrup et al. | |
| 5,653,748 A | 8/1997 | Strecker | |
| 5,683,451 A | 11/1997 | Lenker et al. | |
| 5,690,643 A | 11/1997 | Wijay | |
| 5,690,644 A | 11/1997 | Yurek et al. | |
| 5,702,364 A | 12/1997 | Euteneuer et al. | |
| 5,702,418 A * | 12/1997 | Ravenscroft | 623/1.11 |
| 5,725,549 A | 3/1998 | Lam | |
| 5,725,551 A * | 3/1998 | Myers et al. | 606/213 |
| 5,733,267 A | 3/1998 | Del Toro | |
| 5,733,325 A | 3/1998 | Robinson et al. | |
| 5,772,609 A | 6/1998 | Nguyen et al. | |
| 5,772,668 A | 6/1998 | Summers et al. | |
| 5,772,669 A | 6/1998 | Vrba | |
| 5,776,141 A | 7/1998 | Klein et al. | |
| 5,776,142 A | 7/1998 | Gunderson | |
| 5,782,838 A | 7/1998 | Beyar et al. | |
| 5,788,707 A | 8/1998 | Del Toro et al. | |
| 5,797,857 A | 8/1998 | Obitsu | |
| 5,797,952 A | 8/1998 | Klein | |
| 5,800,455 A | 9/1998 | Palermo et al. | |
| 5,800,517 A | 9/1998 | Anderson et al. | |
| 5,807,398 A | 9/1998 | Shaknovich | |
| 5,810,837 A | 9/1998 | Hofmann et al. | |
| 5,817,101 A | 10/1998 | Fiedler | |
| 5,824,041 A | 10/1998 | Lenker et al. | |
| 5,824,053 A | 10/1998 | Khosravi et al. | |
| 5,824,054 A | 10/1998 | Khosravi et al. | |
| 5,824,058 A | 10/1998 | Ravenscroft et al. | |
| RE35,988 E | 12/1998 | Winston et al. | |
| 5,843,090 A * | 12/1998 | Schuetz | 623/1.11 |
| 5,851,206 A | 12/1998 | Guglielmi et al. | |
| 5,855,578 A | 1/1999 | Guglielmi et al. | |
| 5,873,906 A * | 2/1999 | Lau et al. | 128/898 |
| 5,873,907 A | 2/1999 | Frantzen | |
| 5,891,128 A | 4/1999 | Gia et al. | |
| 5,919,187 A | 7/1999 | Guglielmi et al. | |
| 5,919,204 A | 7/1999 | Lukic et al. | |
| 5,919,225 A * | 7/1999 | Lau et al. | 606/198 |
| 5,920,975 A | 7/1999 | Morales | |
| 5,944,726 A | 8/1999 | Blaeser et al. | |
| 5,948,017 A | 9/1999 | Taheri | |
| 5,957,930 A | 9/1999 | Vrba | |
| 5,968,052 A | 10/1999 | Sullivan, III et al. | |
| 5,980,485 A * | 11/1999 | Grantz et al. | 604/96.01 |
| 5,980,514 A | 11/1999 | Kupiecki et al. | |
| 5,980,530 A | 11/1999 | Willard et al. | |
| 5,984,929 A | 11/1999 | Bashiri et al. | |
| 5,989,242 A | 11/1999 | Saadat et al. | |
| 5,989,280 A | 11/1999 | Euteneuer et al. | |
| 6,004,328 A | 12/1999 | Solar | |
| 6,015,429 A * | 1/2000 | Lau et al. | 623/1.2 |
| 6,019,737 A | 2/2000 | Murata | |
| 6,019,779 A | 2/2000 | Thorud et al. | |
| 6,019,785 A | 2/2000 | Strecker | |
| 6,027,516 A | 2/2000 | Kolobow et al. | |
| 6,027,520 A | 2/2000 | Tsugita et al. | |
| 6,042,588 A | 3/2000 | Munsinger et al. | |
| 6,042,589 A | 3/2000 | Marianne | |
| 6,042,605 A * | 3/2000 | Martin et al. | 623/1.13 |
| 6,048,360 A | 4/2000 | Khosravi et al. | |
| 6,053,940 A | 4/2000 | Wijay | |
| 6,056,759 A | 5/2000 | Fiedler | |
| 6,059,779 A | 5/2000 | Mills | |
| 6,059,813 A | 5/2000 | Vrba et al. | |
| 6,063,101 A | 5/2000 | Jacobsen et al. | |
| 6,063,104 A | 5/2000 | Villar et al. | |
| 6,068,634 A | 5/2000 | Lorentzen Cornelius et al. | |
| 6,068,644 A * | 5/2000 | Lulo et al. | 606/191 |
| 6,071,286 A | 6/2000 | Mawad | |
| 6,077,297 A | 6/2000 | Robinson et al. | |
| 6,093,194 A | 7/2000 | Mikus et al. | |
| 6,096,034 A | 8/2000 | Kupiecki et al. | |
| 6,096,045 A | 8/2000 | Del Toro et al. | |
| 6,102,942 A | 8/2000 | Ahari | |
| 6,113,608 A | 9/2000 | Monroe et al. | |
| 6,117,140 A | 9/2000 | Munsinger | |
| 6,120,522 A | 9/2000 | Vrba et al. | |
| 6,123,714 A | 9/2000 | Gia et al. | |
| 6,123,720 A | 9/2000 | Anderson et al. | |
| 6,126,685 A | 10/2000 | Lenker et al. | |
| 6,139,524 A | 10/2000 | Killion | |
| 6,139,564 A | 10/2000 | Teoh | |
| 6,156,061 A | 12/2000 | Wallace et al. | |
| 6,156,062 A | 12/2000 | McGuinness | |
| 6,161,029 A * | 12/2000 | Spreigl et al. | 600/381 |
| 6,165,178 A | 12/2000 | Bashiri et al. | |
| 6,168,579 B1 | 1/2001 | Tsugita | |
| 6,168,592 B1 | 1/2001 | Kupiecki et al. | |
| 6,168,616 B1 | 1/2001 | Brown, III | |
| 6,168,618 B1 | 1/2001 | Frantzen | |
| 6,174,327 B1 | 1/2001 | Mertens et al. | |
| 6,183,481 B1 | 2/2001 | Lee et al. | |
| 6,183,505 B1 | 2/2001 | Mohn, Jr. et al. | |

| Patent No. | Date | Name |
|---|---|---|
| 6,193,708 B1 | 2/2001 | Ken et al. |
| 6,200,305 B1 * | 3/2001 | Berthiaume et al. .......... 604/509 |
| 6,203,550 B1 | 3/2001 | Olson |
| 6,206,888 B1 | 3/2001 | Bicek et al. |
| 6,214,036 B1 | 4/2001 | Letendre et al. |
| 6,221,081 B1 | 4/2001 | Mikus et al. |
| 6,221,097 B1 | 4/2001 | Wang et al. |
| 6,228,110 B1 | 5/2001 | Munsinger |
| 6,231,597 B1 | 5/2001 | Deem et al. |
| 6,231,598 B1 | 5/2001 | Berry et al. |
| 6,238,410 B1 | 5/2001 | Vrba et al. |
| 6,238,430 B1 | 5/2001 | Klumb et al. |
| 6,241,758 B1 | 6/2001 | Cox |
| 6,245,097 B1 | 6/2001 | Inoue |
| 6,248,122 B1 | 6/2001 | Klumb et al. |
| 6,254,609 B1 | 7/2001 | Vrba et al. |
| 6,254,611 B1 | 7/2001 | Vrba |
| 6,254,628 B1 | 7/2001 | Wallace et al. |
| 6,264,671 B1 | 7/2001 | Stack et al. |
| 6,264,683 B1 * | 7/2001 | Stack et al. .................. 623/1.11 |
| 6,267,783 B1 | 7/2001 | Letendre et al. |
| 6,270,504 B1 | 8/2001 | Lorentzen Cornelius et al. |
| 6,273,881 B1 * | 8/2001 | Kiemeneij .................... 604/532 |
| 6,280,465 B1 | 8/2001 | Cryer |
| 6,287,331 B1 | 9/2001 | Heath |
| 6,302,893 B1 | 10/2001 | Limon et al. |
| 6,306,141 B1 | 10/2001 | Jervis |
| 6,306,162 B1 * | 10/2001 | Patel ............................ 623/1.11 |
| 6,319,275 B1 | 11/2001 | Lashinski et al. |
| 6,342,066 B1 | 1/2002 | Toro et al. |
| 6,344,041 B1 | 2/2002 | Kupiecki et al. |
| 6,346,118 B1 | 2/2002 | Baker et al. |
| 6,350,277 B1 | 2/2002 | Kocur |
| 6,350,278 B1 | 2/2002 | Lenker et al. |
| 6,361,637 B2 * | 3/2002 | Martin et al. ................. 156/187 |
| 6,368,344 B1 | 4/2002 | Fitz |
| 6,371,962 B1 | 4/2002 | Ellis et al. |
| 6,371,979 B1 | 4/2002 | Beyar et al. |
| 6,375,660 B1 | 4/2002 | Fischell et al. |
| 6,379,365 B1 | 4/2002 | Diaz |
| 6,380,457 B1 | 4/2002 | Yurek et al. |
| 6,383,174 B1 | 5/2002 | Eder |
| 6,387,118 B1 | 5/2002 | Hanson |
| 6,391,050 B1 | 5/2002 | Broome |
| 6,391,051 B2 | 5/2002 | Sullivan, III et al. |
| 6,395,017 B1 | 5/2002 | Dwyer et al. |
| 6,409,750 B1 * | 6/2002 | Hyodoh et al. ................. 623/1.1 |
| 6,409,752 B1 | 6/2002 | Boatman et al. |
| 6,413,269 B1 | 7/2002 | Bui et al. |
| 6,416,536 B1 | 7/2002 | Yee |
| 6,416,545 B1 | 7/2002 | Mikus et al. |
| 6,423,090 B1 | 7/2002 | Hancock |
| 6,425,898 B1 | 7/2002 | Wilson et al. |
| 6,425,914 B1 | 7/2002 | Wallace et al. |
| 6,425,915 B1 | 7/2002 | Khosravi et al. |
| 6,428,489 B1 | 8/2002 | Jacobsen et al. |
| 6,428,566 B1 | 8/2002 | Holt |
| 6,432,080 B2 | 8/2002 | Pederson, Jr. et al. |
| 6,432,129 B2 | 8/2002 | DiCaprio |
| 6,447,540 B1 | 9/2002 | Fontaine et al. |
| 6,451,025 B1 | 9/2002 | Jervis |
| 6,451,052 B1 | 9/2002 | Burmeister et al. |
| 6,454,795 B1 | 9/2002 | Chuter |
| 6,458,092 B1 | 10/2002 | Gambale et al. |
| 6,468,266 B1 | 10/2002 | Bashiri et al. |
| 6,468,298 B1 | 10/2002 | Pelton |
| 6,468,301 B1 | 10/2002 | Amplatz et al. |
| 6,482,227 B1 | 11/2002 | Solovay |
| 6,485,515 B2 | 11/2002 | Strecker |
| 6,488,700 B2 | 12/2002 | Klumb et al. |
| 6,514,285 B1 | 2/2003 | Pinchasik |
| 6,517,548 B2 | 2/2003 | Lorentzen Cornelius et al. |
| 6,517,569 B2 | 2/2003 | Mikus et al. |
| 6,520,986 B2 * | 2/2003 | Martin et al. ................. 623/1.13 |
| 6,530,947 B1 | 3/2003 | Euteneuer et al. |
| 6,533,805 B1 | 3/2003 | Jervis |
| 6,533,807 B2 | 3/2003 | Wolinsky et al. |
| 6,537,295 B2 | 3/2003 | Petersen |
| 6,558,415 B2 | 5/2003 | Thompson |
| 6,562,063 B1 | 5/2003 | Euteneuer et al. |
| 6,562,064 B1 | 5/2003 | deBeer |
| 6,579,297 B2 | 6/2003 | Bicek et al. |
| 6,579,308 B1 | 6/2003 | Jansen et al. |
| 6,582,460 B1 | 6/2003 | Cryer |
| 6,602,226 B1 | 8/2003 | Smith et al. |
| 6,602,272 B2 | 8/2003 | Boylan et al. |
| 6,607,539 B1 | 8/2003 | Hayashi et al. |
| 6,607,551 B1 | 8/2003 | Sullivan et al. |
| 6,613,079 B1 | 9/2003 | Wolinsky et al. |
| 6,620,152 B2 | 9/2003 | Guglielmi |
| 6,623,518 B2 | 9/2003 | Thompson et al. |
| 6,626,938 B1 | 9/2003 | Butaric et al. |
| 6,629,981 B2 | 10/2003 | Bui et al. |
| 6,645,237 B2 | 11/2003 | Klumb et al. |
| 6,645,238 B2 | 11/2003 | Smith |
| 6,656,212 B2 | 12/2003 | Ravenscroft et al. |
| 6,660,031 B2 | 12/2003 | Tran et al. |
| 6,660,032 B2 | 12/2003 | Klumb et al. |
| 6,663,660 B2 | 12/2003 | Dusbabeck et al. |
| 6,663,664 B1 | 12/2003 | Pacetti |
| 6,666,881 B1 | 12/2003 | Richter et al. |
| 6,669,719 B2 | 12/2003 | Wallace et al. |
| 6,676,666 B2 | 1/2004 | Vrba et al. |
| 6,679,910 B1 | 1/2004 | Granada |
| 6,689,120 B1 | 2/2004 | Gerdts |
| 6,692,521 B2 | 2/2004 | Pinchasik |
| 6,699,274 B2 | 3/2004 | Stinson |
| 6,702,843 B1 | 3/2004 | Brown et al. |
| 6,702,846 B2 | 3/2004 | Mikus et al. |
| 6,709,425 B2 | 3/2004 | Gambale et al. |
| 6,716,238 B2 * | 4/2004 | Elliott .......................... 623/1.11 |
| 6,726,714 B2 * | 4/2004 | DiCaprio et al. ............. 623/1.11 |
| 6,733,519 B2 * | 5/2004 | Lashinski et al. ............ 623/1.11 |
| 6,736,839 B2 * | 5/2004 | Cummings .................. 623/1.11 |
| 6,802,858 B2 | 10/2004 | Gambale et al. |
| 6,814,746 B2 * | 11/2004 | Thompson et al. .......... 623/1.11 |
| 6,818,014 B2 | 11/2004 | Brown et al. |
| 6,821,291 B2 | 11/2004 | Bolea et al. |
| 6,830,575 B2 | 12/2004 | Stenzel et al. |
| 6,833,002 B2 | 12/2004 | Stack et al. |
| 6,833,003 B2 | 12/2004 | Jones et al. |
| 6,843,802 B1 | 1/2005 | Villalobos et al. |
| 6,858,034 B1 | 2/2005 | Hijlkema et al. |
| 6,860,899 B1 | 3/2005 | Rivelli, Jr. |
| 6,875,212 B2 | 4/2005 | Shaolian et al. |
| 6,878,161 B2 | 4/2005 | Lenker |
| 6,936,058 B2 | 8/2005 | Forde et al. |
| 6,936,065 B2 | 8/2005 | Khan et al. |
| 6,989,024 B2 | 1/2006 | Hebert et al. |
| 7,004,964 B2 | 2/2006 | Thompson et al. |
| 7,011,673 B2 | 3/2006 | Fischell et al. |
| 7,022,132 B2 | 4/2006 | Kocur |
| 7,074,236 B2 | 7/2006 | Rabkin et al. |
| 7,127,789 B2 | 10/2006 | Stinson |
| 7,172,620 B2 | 2/2007 | Gilson |
| 7,300,460 B2 | 11/2007 | Levine et al. |
| 7,393,357 B2 | 7/2008 | Stelter et al. |
| 7,399,311 B2 | 7/2008 | Bertolino et al. |
| 2001/0034548 A1 | 10/2001 | Vrba et al. |
| 2001/0047185 A1 | 11/2001 | Satz |
| 2001/0049547 A1 | 12/2001 | Moore |
| 2001/0049550 A1 * | 12/2001 | Martin et al. ................. 623/1.13 |
| 2002/0002397 A1 * | 1/2002 | Martin et al. ................. 623/1.12 |
| 2002/0032431 A1 * | 3/2002 | Kiemeneij .................... 604/528 |
| 2002/0035393 A1 * | 3/2002 | Lashinski et al. ............ 623/1.11 |
| 2002/0040236 A1 * | 4/2002 | Lau et al. ..................... 623/1.12 |
| 2002/0045928 A1 * | 4/2002 | Boekstegers ................. 623/1.11 |
| 2002/0045930 A1 | 4/2002 | Burg et al. |
| 2002/0049490 A1 | 4/2002 | Pollock et al. |
| 2002/0068966 A1 * | 6/2002 | Holman et al. .............. 623/1.11 |
| 2002/0072729 A1 | 6/2002 | Hoste et al. |
| 2002/0077693 A1 | 6/2002 | Barclay et al. |
| 2002/0095147 A1 * | 7/2002 | Shadduck ........................ 606/41 |
| 2002/0095168 A1 * | 7/2002 | Griego et al. .................. 606/167 |
| 2002/0099433 A1 | 7/2002 | Fischell et al. |
| 2002/0120322 A1 | 8/2002 | Thompson et al. |
| 2002/0120323 A1 | 8/2002 | Thompson et al. |
| 2002/0120324 A1 | 8/2002 | Holman et al. |

| | | | |
|---|---|---|---|
| 2002/0138129 A1* | 9/2002 | Armstrong et al. ......... 623/1.11 |
| 2002/0147491 A1* | 10/2002 | Khan et al. .................. 623/1.11 |
| 2002/0161342 A1 | 10/2002 | Rivelli, Jr. et al. |
| 2002/0169494 A1* | 11/2002 | Mertens et al. .............. 623/1.11 |
| 2002/0188341 A1* | 12/2002 | Elliott ........................... 623/1.1 |
| 2003/0014103 A1 | 1/2003 | Inoue |
| 2003/0018319 A1* | 1/2003 | Kiemeneij ..................... 604/532 |
| 2003/0036768 A1* | 2/2003 | Hutchins et al. .............. 606/170 |
| 2003/0040771 A1* | 2/2003 | Hyodoh et al. ............... 606/200 |
| 2003/0040772 A1* | 2/2003 | Hyodoh et al. ............... 606/200 |
| 2003/0045923 A1 | 3/2003 | Bashiri |
| 2003/0055377 A1* | 3/2003 | Sirhan et al. ............. 604/103.04 |
| 2003/0065375 A1 | 4/2003 | Eskuri |
| 2003/0069521 A1 | 4/2003 | Reynolds et al. |
| 2003/0105508 A1 | 6/2003 | Johnson et al. |
| 2003/0135266 A1 | 7/2003 | Chew et al. |
| 2003/0149467 A1 | 8/2003 | Linder et al. |
| 2003/0163156 A1 | 8/2003 | Hebert et al. |
| 2003/0163189 A1* | 8/2003 | Thompson et al. .......... 623/1.11 |
| 2004/0010265 A1 | 1/2004 | Karpiel |
| 2004/0049547 A1 | 3/2004 | Matthews et al. |
| 2004/0093063 A1 | 5/2004 | Wright et al. |
| 2004/0097917 A1 | 5/2004 | Keane |
| 2004/0127912 A1 | 7/2004 | Rabkin et al. |
| 2004/0193178 A1 | 9/2004 | Nikolchev |
| 2004/0193179 A1 | 9/2004 | Nikolchev |
| 2004/0193246 A1 | 9/2004 | Ferrera |
| 2004/0260377 A1 | 12/2004 | Flomenblit et al. |
| 2005/0049668 A1 | 3/2005 | Jones et al. |
| 2005/0049669 A1 | 3/2005 | Jones et al. |
| 2005/0049670 A1 | 3/2005 | Jones et al. |
| 2005/0080430 A1 | 4/2005 | Wright, Jr. et al. |
| 2005/0096724 A1 | 5/2005 | Stenzel et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209675 A1 | 9/2005 | Ton et al. |
| 2005/0220836 A1 | 10/2005 | Falotico et al. |
| 2005/0246010 A1 | 11/2005 | Alexander et al. |
| 2006/0085057 A1 | 4/2006 | George et al. |
| 2006/0111771 A1 | 5/2006 | Ton et al. |
| 2006/0136037 A1 | 6/2006 | DeBeer et al. |
| 2006/0190070 A1 | 8/2006 | Dieck et al. |
| 2006/0247661 A1 | 11/2006 | Richards et al. |
| 2006/0270948 A1 | 11/2006 | Viswanathan et al. |
| 2006/0271097 A1 | 11/2006 | Ramzipoor et al. |
| 2006/0276886 A1 | 12/2006 | George et al. |
| 2007/0027522 A1 | 2/2007 | Chang et al. |
| 2007/0043419 A1 | 2/2007 | Nikolchev et al. |
| 2007/0073379 A1 | 3/2007 | Chang et al. |
| 2007/0100414 A1 | 5/2007 | Licata et al. |
| 2007/0100415 A1 | 5/2007 | Licata |
| 2007/0100416 A1 | 5/2007 | Licata |
| 2007/0100417 A1 | 5/2007 | Licata |
| 2007/0100418 A1 | 5/2007 | Licata |
| 2008/0015541 A1 | 1/2008 | Rosenbluth et al. |
| 2008/0071309 A1 | 3/2008 | Mazzocchi et al. |
| 2008/0221666 A1 | 9/2008 | Licata et al. |

FOREIGN PATENT DOCUMENTS

| | | |
|---|---|---|
| EP | 0667 132 | 8/1995 |
| EP | 0 747 021 | 12/1996 |
| EP | 1 157 673 | 11/2001 |
| EP | 1518515 | 3/2005 |
| JP | 2002-538938 | 11/2002 |
| WO | WO 97/12563 | 4/1997 |
| WO | WO 97/48343 | 12/1997 |
| WO | WO 98/23241 | 6/1998 |
| WO | WO 99/04728 | 2/1999 |
| WO | WO 99/08740 | 2/1999 |
| WO | WO 00/18330 | 4/2000 |
| WO | WO 00/56248 | 9/2000 |
| WO | WO 01/78627 | 10/2001 |
| WO | WO 03/073963 | 9/2003 |
| WO | WO 03-073963 | 9/2003 |
| WO | WO 2004/087006 | 10/2004 |
| WO | WO 2005/092241 | 10/2005 |
| WO | WO 2005/094727 | 10/2005 |

OTHER PUBLICATIONS

Duerig et al., "An overview of superelastic stent design" *Min Invas Ther & Allied Technol*, 9?3/4):235-246 (2000).

Fischell, M.D. FACC, Tim A., "A Fixed Guidewire Stent Delivery System Rationale and Design" TCT, Washington, D.C. (Sep. 24, 2002).

Rieu et al., "Radial Force of Coronary Stents: A Comparative Analysis" *Catheterization and Cardiovascular Interventions* 46:380-391 (1999).

Stoeckel et al., "A Survey of Stent Designs" *Min Invas Ther & Allied Technol* 11(4):137-147 (2002).

Kandzari et al. "Clinical and Angiographic Efficacy of a Self-Expanding Nitinol Stent in Saphenous Vein Graft Atherslerotic Disease" Am. Heart J 145(5):868-874 (2003).

Welt et al. "Coronary Artery Stents: Design and Biologic Considerations" Cardiology Special Edition 9(2) 9-14(2003).

Definitions of "abut" and "wire"—Random House College Dictionary, 1980, New York, 7 and 510.

International Search Report and Written Opinion of PCT Application No. PCT/US2006/034311, mailed Mar. 22, 2007, 7 pages total.

International Search Report of PCT Application No. PCT/US2006/34130, mailed Nov. 23, 2007, 8 pages total.

International Search Report and Written Opinion of PCT Application No. PCT/US2004/008909, mailed Sep. 24, 2004, 6 pages total.

Supplementary European Search Report of EP Application No. 04758233, mailed Nov. 7, 2007, 7 pages total.

Office Action of Japanese Application No. 2006-507500, mailed Nov. 18, 2009, 9 pages (including English Translation).

Examination Report of Singaporean Application No. 2005050976-1, mailed Feb. 28, 2007, 10 pages total.

Written Opinion of Singaporean Application No. 2005050976-1, mailed Apr. 27, 2006, 9 pages total.

Examination Report of Australian Application No. 2004226464, mailed Jul. 17, 2009, 2 pages total.

International Preliminary Report on Patentability of PCT Application No. PCT/US2006/34130, dated Oct. 14, 2008, 8 pages total.

* cited by examiner

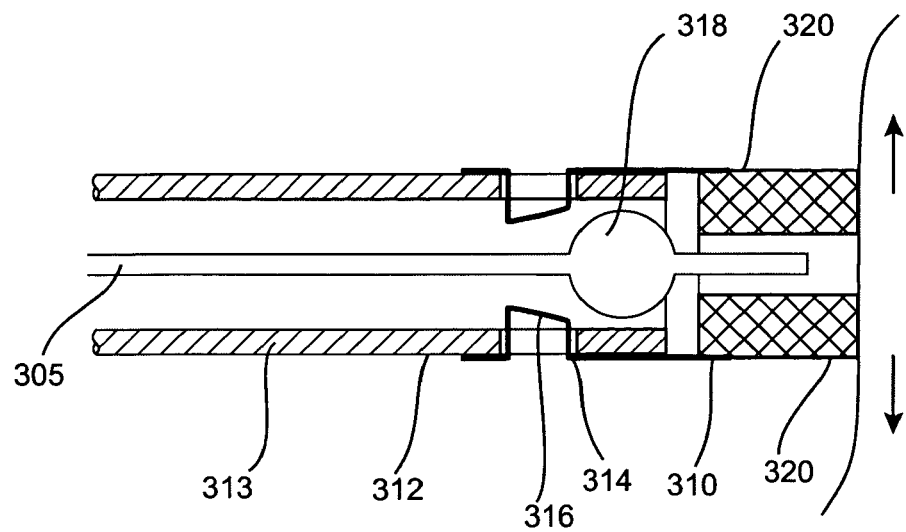
FIG. 3C₁
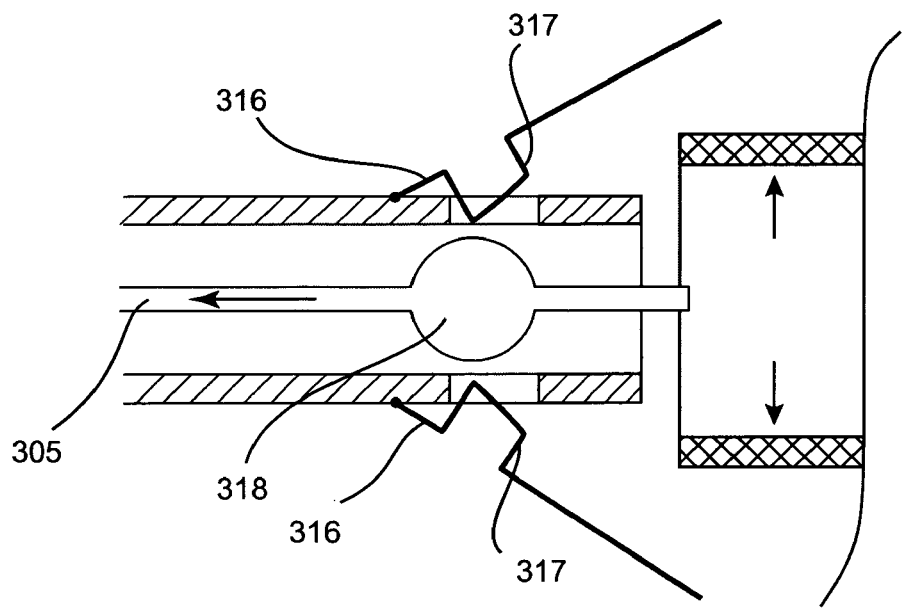
FIG. 3C₂

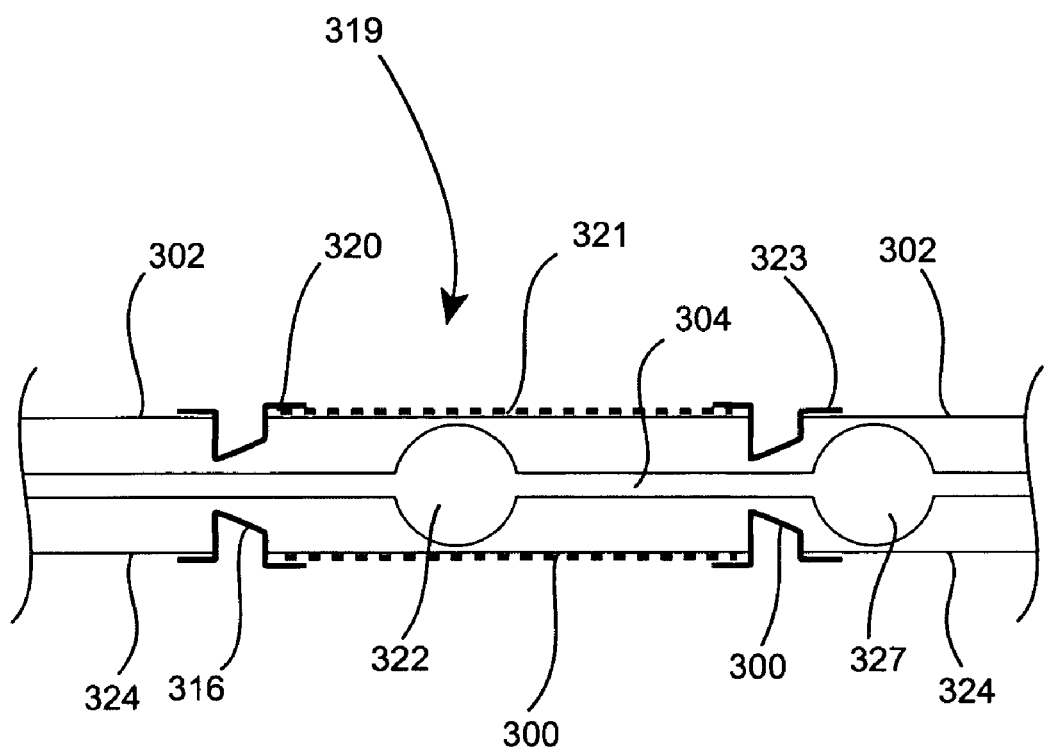
FIG. 3D₁

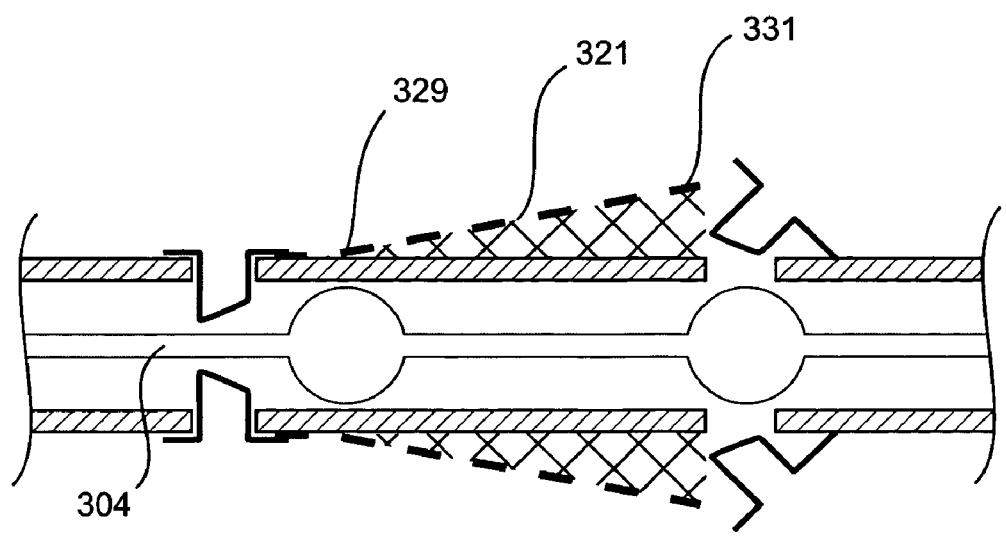
FIG. 3D₂
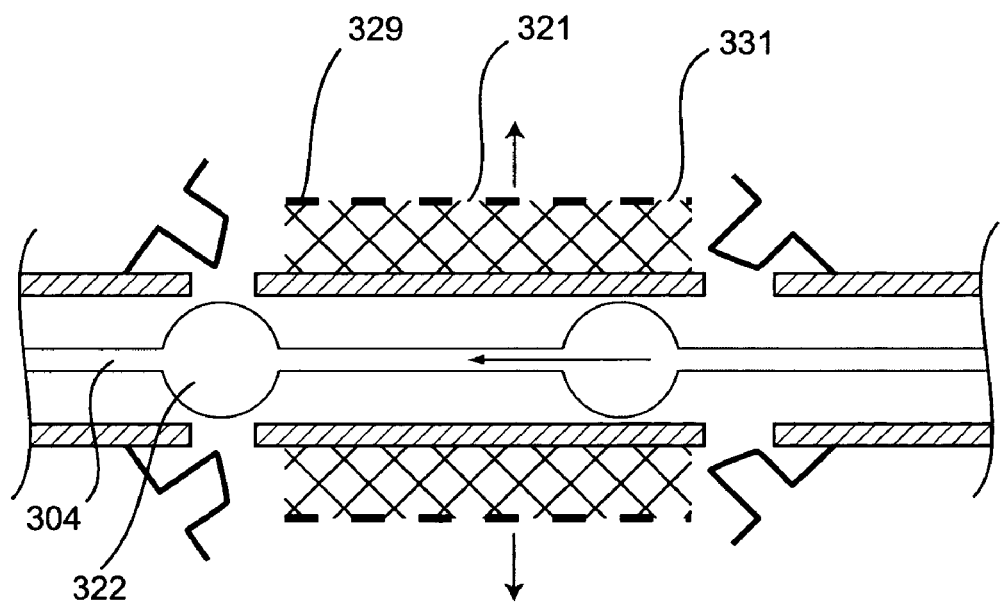
FIG. 3D₃

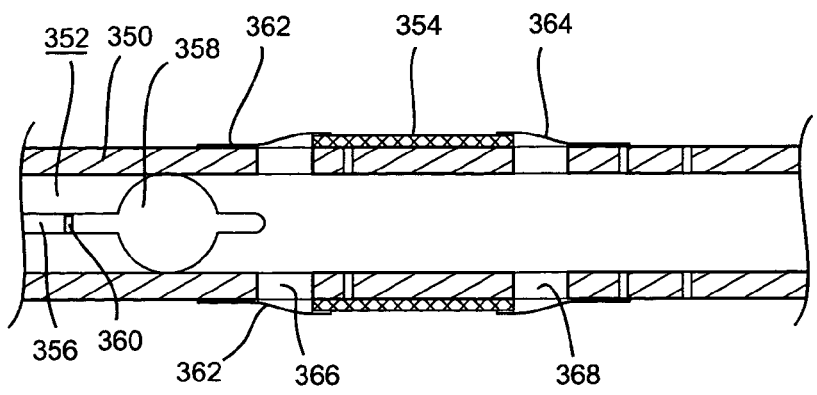
FIG. 3E₁
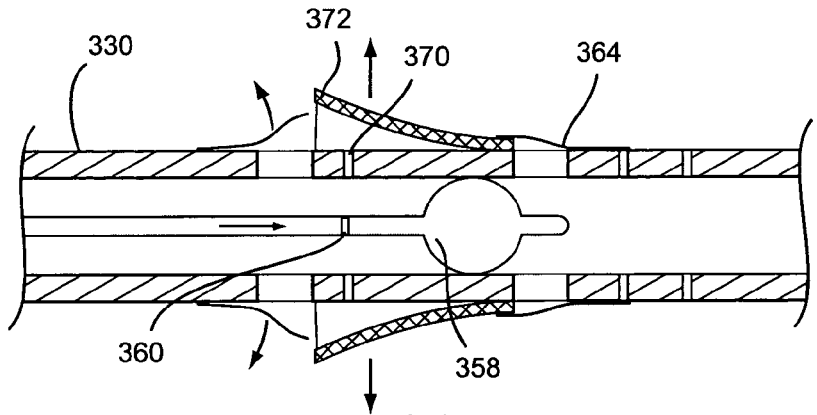
FIG. 3E₂
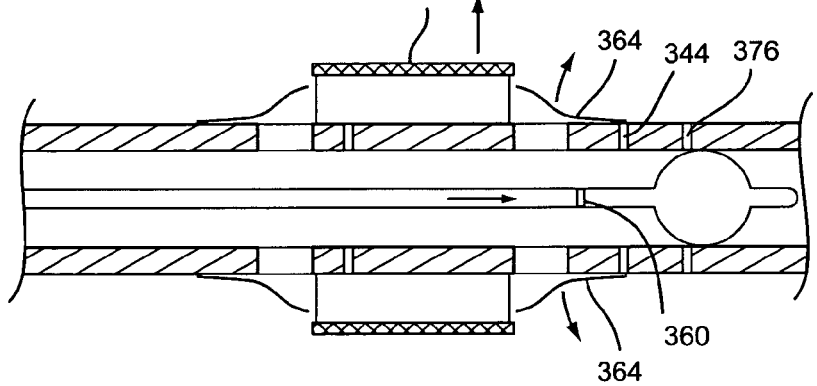
FIG. 3E₃
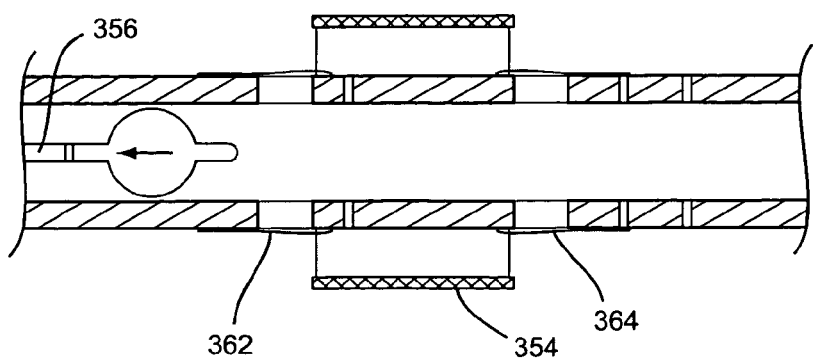
FIG. 3E₄

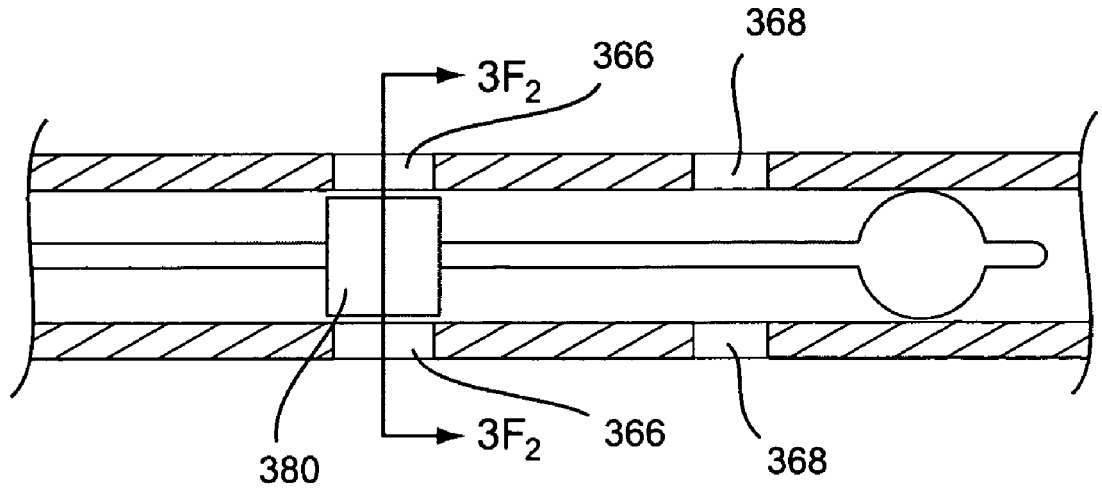
FIG. 3F$_1$
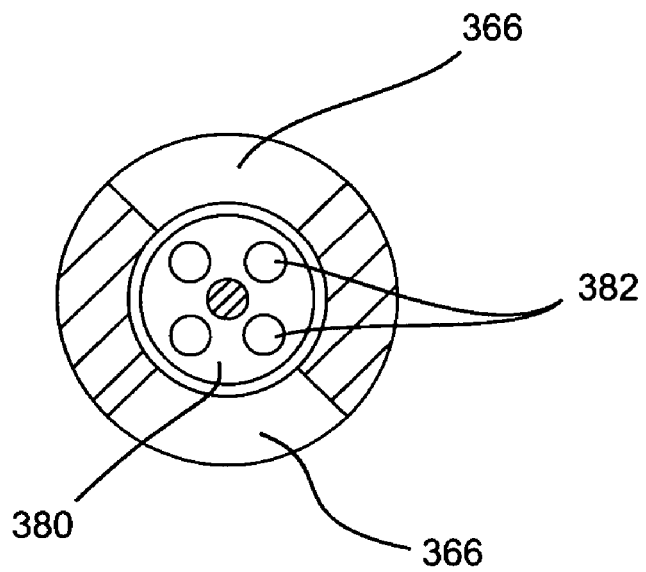
FIG. 3F$_2$

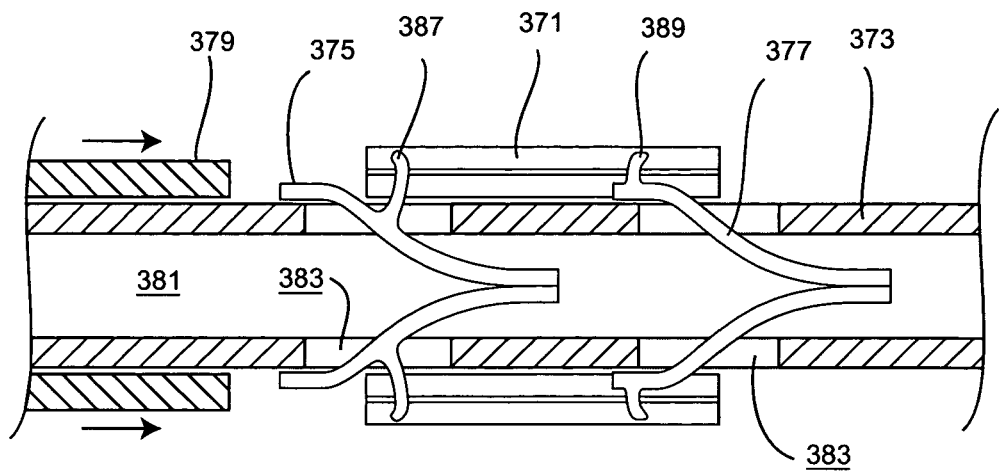
FIG. 3G₁
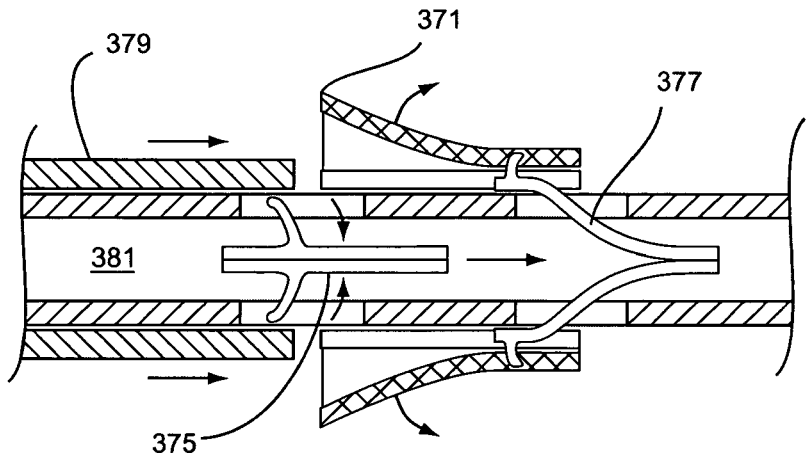
FIG. 3G₂
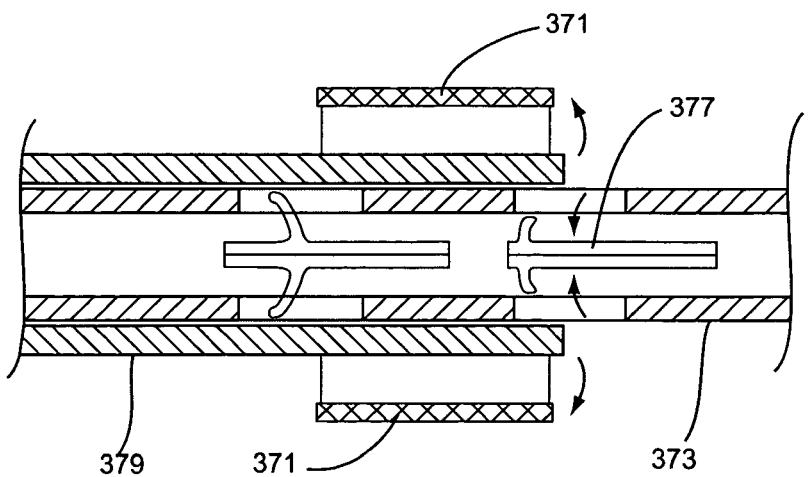
FIG. 3G₃

GUIDEWIRE-LESS STENT DELIVERY METHODS

CROSS REFERENCE TO RELATED APPLICATIONS

This patent claims the benefit of U.S. Provisional Application Ser. No. 60/458,323, entitled, "Implant Delivery Device," filed Mar. 26, 2003 and U.S. Provisional Patent Application Ser. No. 60/462,219, entitled "Implant Delivery Device II", filed Apr. 10, 2003—each by Julian Nikolchev.

FIELD OF THE INVENTION

This invention relates to devices and methods for placing one or more implants such as helical scaffolds or occlusive members into tubular organs or open regions of the body. The implants may be of types that maintain patency of an open anatomical structure, occlude a selected volume, isolate a region, or collect other occlusive members at a site. Included in the description are devices and methods for deploying the various implants, typically without a sheath, in a serial fashion, and with high adjustability.

BACKGROUND OF THE INVENTION

Implants such as stents and occlusive coils have been used in patients for a wide variety of reasons. For instance, stents are often used to treat arterial stenosis secondary to atherosclerosis. Various stent designs have been developed and used clinically, but self-expandable and balloon-expandable stent systems and their related deployment techniques are now predominant. Examples of self-expandable stents currently in use are WALLSTENT® stents (Schneider Peripheral Division, Minneapolis, Minn.) and Gianturco stents (Cook, Inc., Bloomington, Ind.). The most commonly used balloon-expandable stent is the PALMAZ® stent (Cordis Corporation, Warren, N.J.).

Typically, after balloon angioplasty has been performed, either a self-expandable or balloon-expandable stent is advanced over a guidewire and positioned at the target site. A protective sheath or membrane is then retracted proximally to allow expansion of a self-expanding stent. Alternatively, a delivery balloon may be inflated, thereby expanding the stent.

Despite improvements in delivery systems, balloon design, and stent design, these over-the-guidewire and/or sheathed self-expanding stent deployment systems still have their limitations. For instance, sheathed stents tend to move forward when the sheath is pulled back, deploying them imprecisely. The sheathed design also requires that the stent delivery system be larger in diameter and less flexible. Furthermore, for sheathed systems, the interventional procedure may only proceed if the vessel of interest is of sufficiently large diameter to allow sheath placement to avoid significant damage to the luminal surface of the vessel. Moreover, balloon-expandable stents, by virtue of a large diameter and relative inflexibility, are often unable to reach distal vasculature. For both self-expandable and balloon-expandable stent deployment systems, repositioning or step-wise release of the stent are usually not available features. Similarly, occlusive coil placement systems such as systems that deliver detachable platinum coils and GDC® coils also generally do not contain repositionable or step-wise release features.

Consequently, a smaller diameter (lower profile), repositionable implant deployment device that releases an implant into, or upon, a body region in a more precise, continuous or step-wise fashion, without the use of a sheath or balloon would provide significant benefit to patients with various medical conditions.

SUMMARY OF THE INVENTION

The present invention is a low profile implant delivery device that may be deployed without a sheath, and is designed to release portions of implants simultaneously or sequentially.

In one variation, the implant delivery device includes a noninflatable, elongate delivery guide member having a distal end and configuration that allows it to direct at least one implant having an exterior and interior surface to an anatomical treatment site by manipulation by a user. The at least one implant has a delivery diameter prior to its release, is located proximally of the distal end of the delivery guide member prior to release, and has at least one releasable joint configured to maintain at least a section of the at least one implant at the delivery diameter until release of the at least one releasable joint. The delivery guide member sections that are proximal and distal to the at least one implant also have delivery diameters. These guide member delivery diameters may be substantially equal to the at least one implant delivery diameter prior to implant release.

The implant may be a helical scaffold, e.g., a stent, in particular, a self-expandable stent, or it may be an occlusive coil. The implant may be symmetric or asymmetric. In some instances, the implant delivers a therapeutic agent.

The delivery guide member may include a wire and/or a tubular member having a lumen. If desired, a radioopaque marker may be included on the delivery guide to aid with its placement. When designed to include a tubular member, it co-axially surrounds at least a portion of the delivery guide, and words as a tubular actuator configured to release at least one releasable retainer upon distal axial movement along the delivery guide member.

In another variation, the implant delivery device includes an actuator slidably located at least partially within the delivery guide member and is configured to mechanically release at least one releasable retainer upon axial movement of the actuator within the delivery guide member. In other variations, the actuator may also release at least one releasable retainer upon rotational movement of the actuator, upon the application of fluid pressure in the delivery guide member lumen. In another variation, application of a suitable DC current may be employed to at least one releasable joint configured to retain the implant. Release of the releasable retainer using any one of the release mechanisms, described above may be sequential, if precise positioning is required, or may be simultaneous. Each feature of each variation may be used on any of the other, variations.

The implant delivery device may be included in a system for implant delivery which further employs one or more embolic filters at either the proximal or distal section of the delivery guide, or at both the proximal and distal sections of the delivery guide.

The system may be used for implant delivery into lumens of tubular organs including, but not limited to, blood vessels (including intracranial vessels, large vessels, peripheral vessels, adjacent aneurysms, arteriovenous malformations, arteriovenous fistulas), ureters, bile ducts, fallopian tubes, cardiac chambers, ducts such as bile ducts and mammary ducts, large and small airways, and hollow organs, e.g., stomach, intestines, and bladder. The implant may be of a design that is of a size that is smaller during delivery and larger after implantation. The design may be used to provide or to maintain patency in an open region of an anatomical structure, or to occlude a site, or to isolate a region (e.g., to close an aneurysm by blocking the aneurysm opening or neck by placement in an adjacent anatomical structure such as an artery or gastrointesinal tubular member), or to corral or collect a number of occlusive devices (e.g., coils or hydratable polymeric noodles) or compositions at a site to be occluded or supported. In another variation, the implant is located in a gap between proximal and distal sections of the delivery guide member. The system may also be employed for implant delivery into solid organs or tissues including, but not limited to, skin, muscle, fat, brain, liver, kidneys, spleen, and benign and malignant tumors. Preferably, the implant is delivered to a target site in a blood vessel lumen.

In a general aspect, the system is a guidewire-less implant delivery system that includes a noninflatable, elongate delivery guide member having a proximal end and a distal end. The guide member is configured to direct at least one implant having an exterior and interior surface to an anatomical treatment site by manipulation by a user. The at least one implant has a delivery diameter prior to release of the at least one implant and is located proximally of the distal end of the delivery guide member prior to release. The at least one releasable retainer or electrolytic joint is configured to maintain at least a section of the at least one implant at the delivery diameter until release of the at least one respective member(s). The guidewire-less system also has a flexibility and remote directability such that a user may direct the distal end of the guide member into, and introduce, the at least one implant into a coronary artery solely by manipulation of the delivery guide member from its proximal end.

BRIEF DESCRIPTION OF THE DRAWING(S)

FIGS. $3C_1$ and $3C_2$ are longitudinal cross-sectional views of an implant delivery device having a mechanical release mechanism for deploying one end of an implant.

FIGS. $3D_1$-$3D_3$ are longitudinal cross-sectional views of an implant delivery device having a mechanical release mechanism for independently releasing the implant ends.

FIGS. $3E_1$-$3E_4$ are longitudinal cross-sectional views of an implant delivery device having a hydraulic release mechanism for independently releasing the implant ends.

FIGS. $3F_1$-$3F_2$ are longitudinal cross-sectional views of a variation of the hydraulic release mechanism described in $3E_1$-$3E_4$.

FIGS. $3G_1$-$3G_3$ are longitudinal cross-sectional views of an implant delivery device having a mechanical release mechanism according to another variation of the invention.

Figure 4:
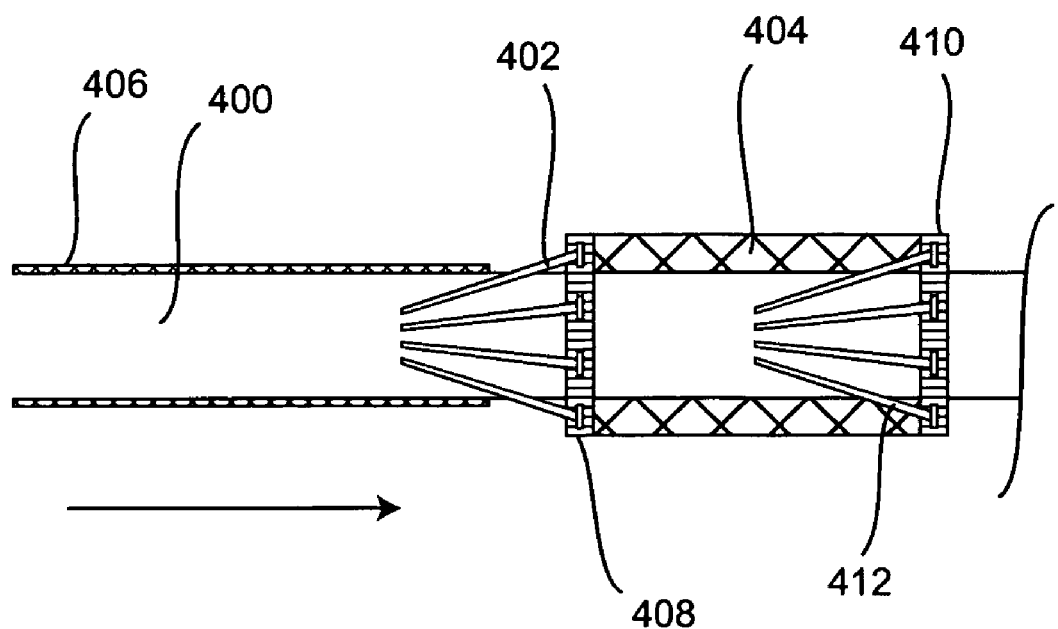

FIG. 4 is a longitudinal cross-sectional view of an implant delivery device having a mechanical release mechanism according to yet another variation of the invention.

Figure 5A:
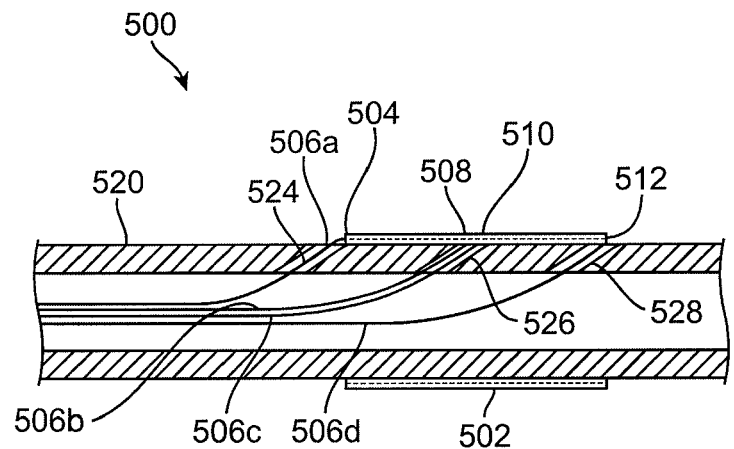
Figure 5B:
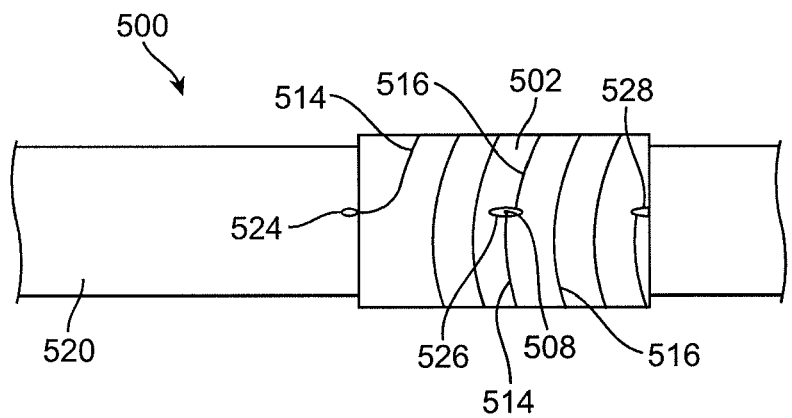
Figure 5C:
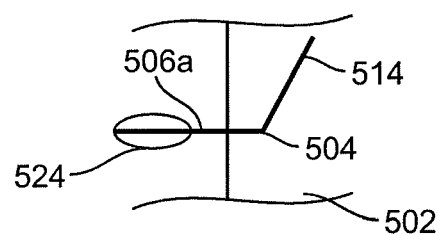

FIGS. 5A-5C are longitudinal cross-sectional views of an implant delivery device having an electrolytic implant release mechanism.

Figure 5D:
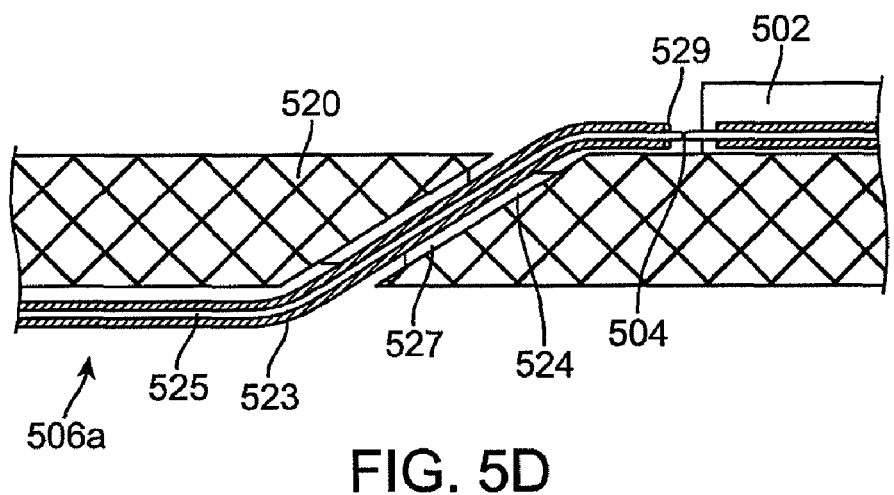

FIG. 5D shows a longitudinal cross-sectional view of an implant delivery device having an electrolytic release mechanism according to another variation of the invention.

Figure 5E:
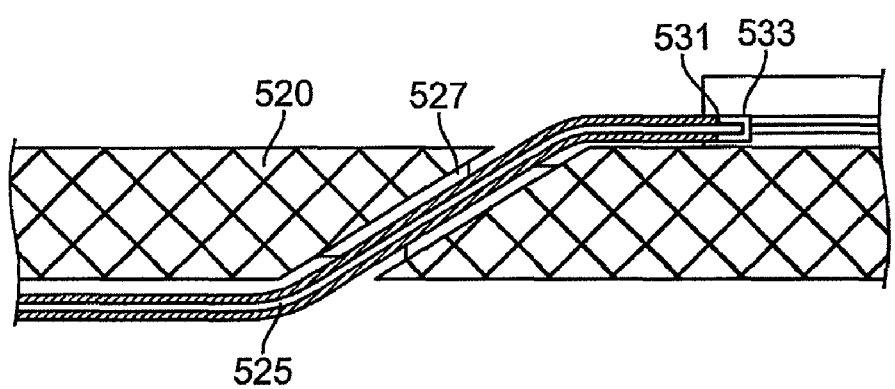

FIG. 5E shows a longitudinal cross-sectional view of an implant delivery device having a thermal release mechanism according to one variation of the invention.

FIGS. 6A-6D show the general method for serially releasing an implant at a target site.

DETAILED DESCRIPTION OF THE INVENTION

Described here are devices, systems, and methods for delivering implants into both open and solid regions of the body. The term "region" as used herein refers to luminal structures as well as solid organs and solid tissues of the body, whether in their diseased or nondiseased state. Examples of luminal structures include, but are not limited to, blood vessels, arteriovenous malformations, aneurysms, arteriovenous fistulas, cardiac chambers, ducts such as bile ducts and mammary ducts, fallopian tubes, ureters, large and small airways, and hollow organs, e.g., stomach, intestines, and bladder. Solid organs or tissues include, but are not limited to, skin, muscle, fat, brain, liver, kidneys, spleen, and benign and malignant tumors.

The device assembly generally includes an elongate, perhaps solid delivery guide, an implant, and one or more implant release mechanisms. Guidewire-less systems are used to deliver the one or more implants. By "guidewire-less" it is meant that the system does not require a guiding device of a diameter less than that of the guide member upon which the implant is delivered to reach a chosen implantation site. Instead, the guidewire-less system is flexible and remotely directable, the remote directability being such that a user may direct the distal end of the guide member into, and introduce, the at least one implant into a coronary artery solely by manipulation of the delivery guide member from its proximal end.

Delivery Guide or Delivery Guide Member

The delivery guide is elongate and has a comparatively small effective diameter. It has the function of permitting delivery of the implant to a selected site and supporting the implant in a collapsed form during positioning and implantation. The delivery guide is usually noninflatable. It may also be solid, or may have a lumen extending therethrough, depending on such factors as the degree of flexibility required, type of associated release mechanism, the constitution material, and the like. The tip of the delivery guide may be tapered and/or straight, curved, or j-shaped, depending on factors such as physician preference, the anatomy of the tubular organ or region of interest, degree of stiffness required, and the like. The delivery guide may or may not include an outer spring coil, for, e.g., fluoroscopic visualization.

The delivery guide member and the delivery system into which it is placed desirably serves the function as would a guidewire in, for instance, a cardiac or neurovascular catheterization procedure. The concept that the delivery guide member or system including that guide member and implant(s) is "remotely directable" is to say that the combination of physical parameters of the delivery guide member, implant, and joints are selected to allow advancement of the system much in the same way as would be a guidewire. Such physical parameters include, for instance, choice of materials, stiffness, size of materials, physical or chemical treatment, tapering (if desired), all in the same way that those physical parameters are selected in designing a cardiovascular or neurovascular guidewire.

The delivery guide may be made from any biocompatible material including, but not limited to, stainless steel and any of its alloys; titanium alloys, e.g., nickel-titanium alloys; other shape memory alloys; tantalum; polymers, e.g., polyethylene and copolymers thereof, polyethylene terephthalate or copolymers thereof, nylon, silicone, polyurethanes, fluoropolymers, poly (vinylchloride), and combinations thereof. The diameter of the delivery guide may usually be about 0.013 cm to about 0.130 cm (about 0.005 inches to about 0.05 inches), more usually about 0.013 cm to about 0.076 cm (about 0.005 inches to about 0.03 inches), and more usually still about 0.015 cm to about 0.030 cm (about 0.006 inches to about 0.012 inches). In a preferred variation, the diameter of the delivery guide is approximately about 0.020 cm (about 0.008 inches).

A lubricious coating may be placed on the delivery guide if desired to facilitate advancement of the delivery guide. The lubricious coating typically will include hydrophilic polymers such as polyvinylpyrrolidone-based compositions, fluoropolymers such as tetrafluoroethylene, or silicones. In one variation, the lubricious coating may constitute a hydrophilic gel. Furthermore, the delivery guide may include one or more radioopaque markers that indicates the location of the distal section of the delivery guide upon radiographic imaging. Usually, the marker will be detected by fluoroscopy.

Implants

The implant itself may be of a shape tailored to achieve a specific purpose. As noted elsewhere, if the purpose of the implant is to provide or to maintain patency of an anatomical structure such as an artery or duct, the implant shape after implantation is itself tubular. The shape may be symmetric or asymmetric, as the purpose dictates.

Other shapes, including cage structures, may be used to provide patency to vessels or to act as collecting or coralling structures for occlusive members or materials.

If the purpose or task is to occlude a lumen or open region, the implant may have the form of an occlusive coil that remains helical after deployment or assumes a random orientation.

In one variation, the implant for placement into a luminal structure is a helical scaffold, e.g., a stent, but any scaffold shape that maintains patency of a lumen may be used. The stents are typically self-expanding stents, such as described in U.S. Pat. No. 4,768,507 to Fishell et al., U.S. Pat. No. 4,990,155 to Wilkoff et al., and U.S. Pat. No. 4,553,545 to Maass et al. In another variation, the implant is an occlusive member, e.g., an occlusive coil, such as described in U.S. Pat. No. 5,334,210 to Gianturco and U.S. Pat. No. 5,382,259 to Phelps et al.

The interior and exterior surfaces of the implant may be designed to prevent the activation of pathological processes during or after implant deployment. For example, in the case of a vascular stent, the exterior stent surface may be formed to be smooth to decrease the likelihood of intimal damage upon stent release (which would trigger the inflammatory process and attract atheromatous plaque-forming cells). The interior stent surface may also be smooth to minimize turbulent flow through the stent and decrease the risk of stent thrombosis.

Important physical properties of the implant to consider include, but are not limited to: length, (stent) diameter in the expanded state, degree of flexibility and lateral stiffness, and the like. These physical properties will be modified to account for such factors as lumen diameter, length of any stenosis, type of luminal structure, or solid organ or tissue involved.

Metals such as stainless steel and tantalum, or metal alloys such as alloys of nickel and titanium, specifically including superelastic alloys such as NITINOL or Elgiloy which are commonly used by those of skill in the art, may be used to form the implants. However, the implants may also be made from biodegradable polymers, e.g., copolymers of lactic and glycolic acid, or nonbiodegradable polymers, e.g., copolymers of ethylene and vinyl acetate.

The implants may also include a therapeutic agent. Examples of therapeutic agents that may be used in the implants include, but are not limited to, antibiotics, anticoagulants, antifungal agents, anti-inflammatory agents, antineoplastic agents, antithrombotic agents, endothelialization promoting agents, free radical scavengers, immunosuppressive agents, thrombolytic agents, and any combination thereof. If the implant is a stent, an antithrombotic agent is preferably included.

Examples of selective antithrombotic agents include acetylsalicylic acid, argatroban, cilostazol, copidogrel, cloricromen, dalteparin, daltroban, defibrotide, dipyridamole, enoxaparin, epoprostenol, indobufen, iloprost, integrelin, isbogrel, lamifiban, lamoparan, nadroparin, ozagrel, picotamide, plafibride, reviparin sodium, ridogrel, sulfinpyrazone, taprostene, ticlopidine, tinzaparin, tirofiban, triflusal, and any of their derivatives.

The therapeutic agent may be coated onto the implant, mixed with a biodegradable polymer or other suitable temporary carrier and then coated onto the implant, or, when the implant is made from a polymeric material, dispersed throughout the polymer.

The implant may include a radioactive material. The radioactive material may be selected on the basis of its use. For instance, the material may be included in an implant where the implant is in the form of a stent that is to be situated over a vascular stenosis. The radioactivity lowers the incidence of re-stenosis. Additionally, the radioactivity may serve the function of a tracer, to allow detection of the location of the implant during the procedure or anytime thereafter. Suitable radioactive tracers include isotopes of gallium, iodine, technetium, and thallium.

Release Mechanism

Figure 1A:
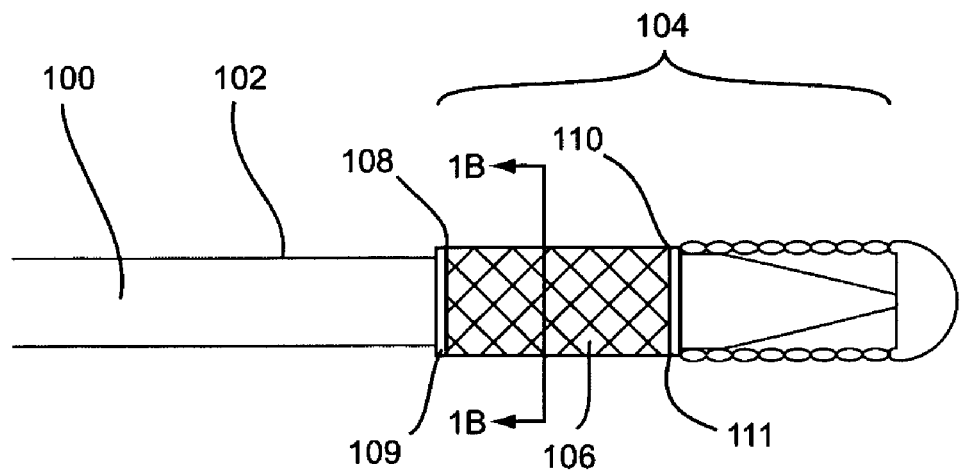
FIG. 1A is a side view of an implant delivery device with a partial cross-section of the distal section of the delivery guide.
Figure 1B:
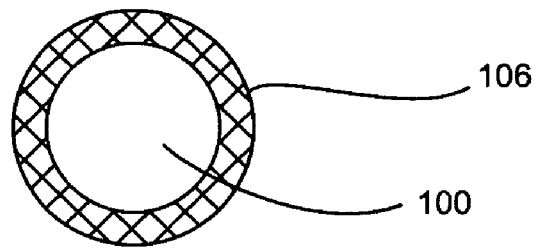
FIG. 1B is a cross-sectional view of the delivery guide and implant taken at line 1B-1B in FIG. 1A.

In one variation of the generic implant delivery system, as shown in FIG. 1A, the implant delivery system includes a delivery guide 100. Delivery guide 100 has a proximal section 102 and a distal section 104. An implant, in this case depicted as a stent 106, surrounds a portion of the distal section 104 of the delivery guide, and is releasably attached to the distal section 104 of the delivery guide. The implant 106, as shown in FIG. 1B, is concentrically adjacent to the delivery guide 100. Although I show the stent in FIGS. 1A and 1B as the implant (106), I depict it in this fashion solely for the illustrative purpose of indicating the siting of the implant 106 on the delivery guide 100 with the distal and proximal implant release mechanism (109, 111). Various implant release mechanisms or structures are discussed in greater detail below.

Implant 106 is shown to be directly attached to, is contiguous to, the delivery guide 100 at the proximal end 108 of the implant and distal end 110 of the implant. In the system shown in FIG. 1A, implant 106 may be secured to the delivery guide 100 by such generic controllably releasable mechanisms as mechanical, thermal, hydraulic, and electrolytic mechanisms, or a combination thereof. Examples of these release mechanisms will be discussed below.

Consequently, release of the implant 106 from the delivery guide 100 may be achieved through a mechanical detachment process involving, e.g., twisting of the delivery guide, such as described by Amplatz in U.S. Pat. No. 6,468,301, or translational movement of the delivery guide in relation to the implant. Implant release may also be achieved using a thermally detachable joint, such as described in U.S. Pat. No. 5,108,407 to Geremia et al., an electrolytic detachable joint, such as described in U.S. Pat. No. 5,122,136 and U.S. Pat. No. 5,354,295, both to Gulglielmi et al., or a combination thereof.

Figure 2:
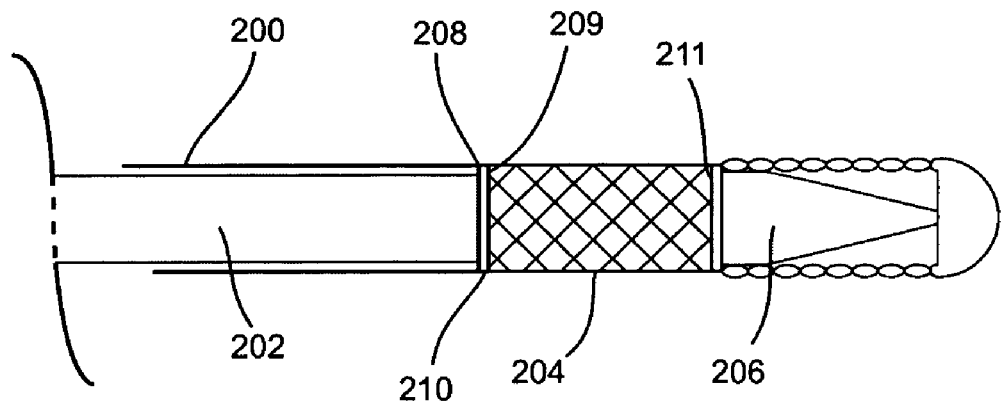
FIG. 2 is a side view of an implant delivery device having a tubular member (actuator) attached to the proximal implant end with a partial cross-section of the distal section of the delivery guide.

In another variation, and as shown in FIG. 2, the system includes a tubular member 200 co-axially mounted on a delivery guide 202. Tubular member 200 may form a component of the delivery guide 202 that cooperates with one or more of the releasable mentioned joints on the implant (209, 211) to release those joints (and therefore, release the implant 204) upon application of a releasing movement, axial or twisting. An implant, e.g., a stent 204, is mounted on a distal section 206 of the delivery guide and the distal end 208 of the tubular member is attached to the proximal end 210 of the stent. The distal end 212 of the stent is attached using a releasable joint 211 to the distal section 206 of the delivery guide 202.

Figure 3A:
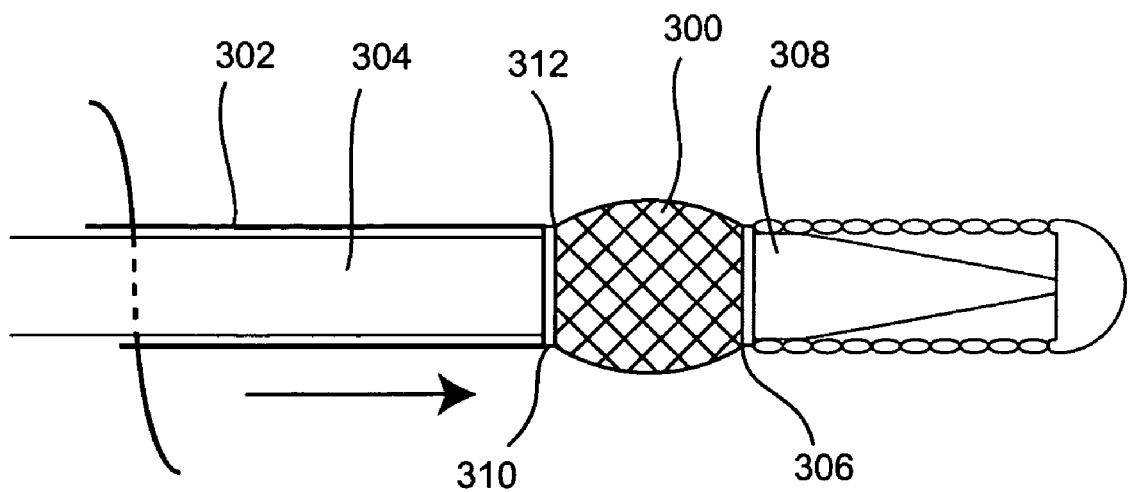
FIG. 3A is a side view of the implant in FIG. 2 being expanded by distally moving the tubular member towards the distal section of the delivery guide.

As mentioned above, I may use a tubular member mounted coaxially about the delivery guide, that slides axially about that delivery guide, as a actuator to release the implant. The outer tubular member may also be used to pre-position the implant. For instance, prior to release, the outer tubular member may be used to expand the implant to therefore obscure its placement, and so to permit adjustment of the placement. FIG. 3A shows a stent 300 expanding as tubular member 302 is moved distally on the delivery guide 304, in the direction of the arrow. The stent is then released from the delivery guide. Specifically, the distal end 306 of the stent is released from a distal section 308 of the delivery guide, followed by release of the proximal end 310 of the stent from the distal end 312 of the tubular member. As mentioned above, the stent 300 may be secured to a distal section 308 of the delivery guide by such mechanisms as lock and key arrangements, biocompatible adhesives, soldering, or a combination thereof. Consequently, stent release may be achieved through a mechanical detachment process, a thermal detachment process (e.g., by heat produced from an exothermic reaction), an electrolytic detachment process, or a combination thereof.

Figure 3B:
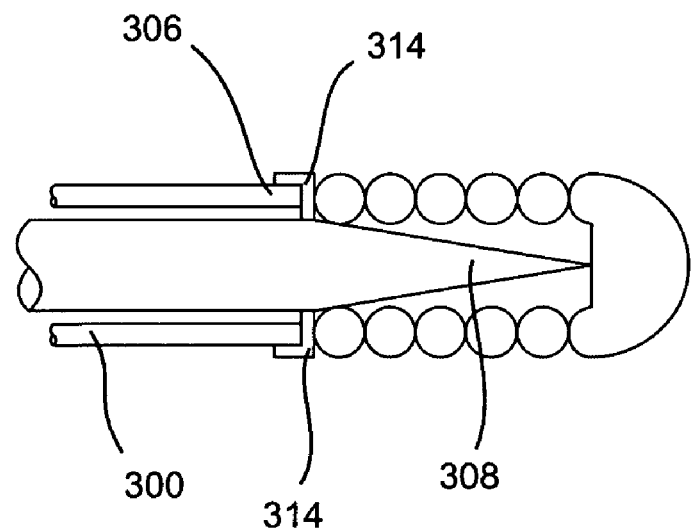
FIG. 3B is a longitudinal cross-sectional view of a distal implant release mechanism.

FIGS. 3B and 3C show yet another variation of a stent release mechanism. In FIG. 3B, brackets 314 may be used to couple the stent 300 to the distal section 308 of the delivery guide. Separation of the stent 306 from the brackets 314, e.g., by one of the detachment processes mentioned above, releases the distal end 306 of the stent from a distal section 308 of the delivery guide, allowing the stent distal end 306 to expand in the tubular organ.

Controllable release of an end of an implant from the delivery guide may be accomplished using the structure of FIG. $3C_1$. Brackets 314 couple the stent proximal end 310 to the distal region 312 of the tubular member 313 that forms a portion of the delivery guide. The brackets 314 have a ramped region 316 which are proximally adjacent to an enlarged (and perhaps ball- or barrel-shaped) portion 318 of the delivery guide and bracket arms 320. The delivery guide and stent each have a delivery diameter, and these delivery diameters may be substantially equal prior to release of the stent. When the actuator 305 is moved proximally, as shown by the direction of the arrow, the ball-shaped portion 318 forces the ramped regions 316 of the brackets outward from the delivery guide axis, in a radial fashion, causing the bracket arms 320 to be displaced radially outwardly from the proximal end 310 of the stent, thereby releasing the stent proximal end 310.

FIG. $3C_2$ shows the results of moving the actuator 305 proximally. The clips (316) have rotated as shown due to the force exerted upon the ramps (317) by the ball (318). The implant (320) has expanded in diameter from that found in its undelivered form.

The actuator may be attached, perhaps with a distal radioopaque coil or directly, to a distal section (not shown) of the guide member.

FIG. $3D_1$, shows a delivery system 319 in which the two ends of the implant 321 may be independently deployed by using an actuator 304 having a proximal releasing ball 322 and a distal releasing ball 327. The implant 321 is located in a gap between sections of the delivery guide and are releasably attached to the delivery guide by brackets or clips. The two balls are spaced in such a way that, in the variation shown in FIG. $3D_1$, the distal ball 327 releases the distal end 331 of implant 321 and the proximal ball 322 then releases the proximal end 329 of implant 321 upon additional proximal movement of actuator 304. This sequence of events is shown in FIGS. $3D_1$, $3D_2$, and $3D_3$. The implant 321, is shown to be completely released in FIG. $3D_3$. In this variation, the implant 321 may be self-expanding, e.g., constructed of a superelastic alloy such as nitinol or another alloy having high elasticity, e.g., an appropriate stainless steel.

A structure similar to that shown in FIGS. $3D_1$, $3D_2$, and $3D_3$ may also be used to deploy an implant using fluid pressure as the releasing impetus.

FIGS. $3E_1$, $3E_2$, $3E_3$ and $3E_4$ show a hydraulic variation. Shown are the delivery guide 350, having a hollow lumen 352, a self-expanding implant 354 (shown variously as non-expanded (e.g., in a "first form") in FIG. $3E_1$, partially expanded in FIG. $3E_2$, and fully expanded in FIGS. $3E_3$ and $3E_4$ (e.g., in a "second form")), and an actuator 356 with a sealing member 358 and a radio-opaque member 360.

The implant 354 (here shown to be a stent or the like) is held to the delivery guide 350 during delivery to the selected treatment site using distal brackets 364 and proximal brackets 362 or clips or the like. The proximal and distal brackets (364, 362) either include regions that cooperate with the fluid in lumen 352 to move upon application of increased pressure in that lumen 352 and release the implant 350 or move in concert with a separate pressure sensitive motion component.

FIG. $3E_1$ shows the actuator 356 as the sealing member 358 approaches the various orifices or openings (proximal orifices 366 and distal orifices 368) communicating from the lumen 356 to the hydraulically or fluidly actuatable clips or retaining brackets (proximal brackets 362 and distal brackets 364).

Included in the description of this variation is a radio-opaque marker 360 on the actuator shaft 356 that allows the user to simply line up that actuator marker 360 with a corresponding radio-opaque marker 370 or the delivery guide 350, increase the pressure in lumen 352 (via syringe, pump, etc.) and deploy the proximal end 371 of implant 354. The interior pressure raises or rotates the proximal clips or brackets 362 and moves them out of contact with the implant 354. FIG. $3E_2$ shows the movement of the proximal end of implant 354 away from the delivery guide 350.

FIG. $3E_3$ shows the axial movement of actuator 356 distally to a position where the sealing member 358 is positioned to actuate distal clips or brackets 364 and release the distal end of implant. Again, a radio-opaque marker 374 (perhaps with an additional identification band 376) has been depicted to show alignment of the radio-opaque marker or band 360 on the actuator shaft 356 prior to the increase in pressure for deployment.

FIG. 3E₄ shows final deployment at the implant 354 and proximal movement at the actuator 356, just prior to withdrawal of the delivery guide 350. The distal and proximal clips or brackets (362, 364) have relaxed to the surface of the delivery guide 350.

Alternatives to certain of the elements shown in the variation found in FIGS. 3E₁ to 3E₄ is seen in FIGS. 3F₁ and 3F₂ and includes, e.g., a cover element 380 to block or cover proximal orifices 366 during the pressurization of the distal orifices 368. The cover element 380 includes holes 382 to allow fluid flow past the cover element 380.

FIG. 3G₁ shows a variation of the described system in which an implant or stent 371 is maintained in position on a hollow delivery guide 373 using spring clips 375 proximally and 377 distally. The spring clips hold the implant 371 in place during delivery and against guide member 373. An actuator 379 is used to remove the clips 375, 377 sequentially and to release each end of implant 371 in an independent fashion. Clips 375 and 377, after actuation or release, remain interior to the guide member 373 for later removal with that guide member. The system shown in FIGS. 3G₁, 3G₂ and 3G₃ may be used to deliver a number of implants in a sequential fashion. Since the retainer clips 375, 377 remain within the guide member 373 after delivery, the actuator 379 is able to slide past the site on guide member 373 where the clips 375, 377 resided prior to implant 371 deployment, down to and distally to a site on the guide member having another implant for subsequent delivery. Consequently, an arrangement such as this may be used to deploy, in a sequential fashion, a number of stents or the like without withdrawal of the guide member.

In the variation shown in FIGS. 3G₁, 3G₂ and 3G₃, the clips 375 and 377 are spring-biased to collapse within the lumen 381 of the guide member 373 once they are pushed into the respective slots 383 provided for such retraction. Such spring loaded clips retain the self expanding stent or implant 371 onto the face of guide member 373. Each of clips 375, 377 are shown in this variation to have hook members 387, 389 that engage the implant 371, often axially stretching the implant 371 and maintaining the delivery radius of the implant 371 as shown.

As shown in FIG. 3G₁, actuator 379 is pushed distally along the outer surface of guide member 373 until it contacts the proximal end of clip 375. Further distal movement of actuator 379 urges clip 375 into lumen 381 thereby rotating horn 387 out of cooperating receptacle area in implant 371.

FIG. 3G₂ shows the results of such movement after clip 375 has completed its springed closure within lumen 381. As shown in that Figure, the proximal end of implant 371 has expanded and yet the distal end of implant 371 remains closed and hooked to distal clip 377. This semi-open condition allows for some adjustment of the implant if needed. FIG. 3G₃ shows the results of additional distal movement of actuator 379 until it contacts distal clip 377 (shown in FIG. 3G₃ in its collapsed form) and thereby allowing the distal end of implant 371 to self-expand into the chosen treatment site.

FIG. 3G₃ shows that guide member 379 is free. Implant 371 is shown in its self expanded form no longer adjacent the central guide member 379. Actuator 379 is situated within implant 371 and is no longer in contact with proximal clip 375 nor distal clip 377. Actuator 379 is thus able to continue distally to another implant containing site positioned in a more distal site on the guide member 373.

The mechanical variation shown in FIGS. 3G₁, 3G₂, 3G₃ may be modified in such a way that the actuator is interior to the lumen of the guide member and deploys the implant upon distal movement of the actuator by providing an actuator with a slot or other "room-making" provisions in the actuator. The actuator and any retained clips would then be used to actuate the clips in the next more distal implant if so desired.

In yet a further variation, the system releases an implant (shown as a stent 404 in FIG. 4) attached to a delivery guide 400 by one or more attachment arms 402 positioned, e.g., at the implant proximal and distal ends, by sliding a tubular member 406, mounted co-axially on the delivery guide 400, distally over the delivery guide 400. The stent 404 is secured to the delivery guide 400 when the attachment arms 402 are in a radially expanded configuration (as illustrated in FIG. 4). The tubular member 406 urges the attachment arms 402 into a compressed configuration as it slides distally over the delivery guide 400, in the direction of the arrow. When the attachment arms 402 are compressed by the tubular member 406, they are moved inward from the stent 404, toward the central axis of the delivery guide 400, thereby releasing the stent 404 from the delivery guide 400. Stent detachment occurs in a serial fashion as the tubular member 406 is moved distally, with detachment of the stent proximal end 408 occurring before detachment at the stent distal end 410. Consequently, if the stent position requires readjustment after detachment of the stent proximal end, the stent may be repositioned prior to detaching the stent distal end. In one variation, the tubular member is a balloon catheter.

The attachment arms 402 are generally made from the same materials as the delivery guide 400, e.g., stainless steel or nickel-titanium alloy, and will typically have a length, thickness, shape, and flexibility appropriate for its intended mechanism of release. The distal ends 412 of the attachment arms may be of any design, so long as one or more of them, when in a radially expanded configuration, secures a portion of a stent to a delivery guide, and when in a compressed configuration, releases that same stent portion from the delivery guide.

The tubular member may be a thin-walled tube (e.g., approximately 0.005 cm (0.002 inches) in thickness) with an outside diameter ranging from about 0.025 cm to about 0.139 cm (0.010 inches to about 0.055 inches), more usually from about 0.025 cm to about 0.05 cm (0.010 inches to about 0.020 inches), and more usually still from about 0.025 cm to about 0.035 cm (0.010 inches to about 0.014 inches). Depending on such factors as degree of flexibility or durometer required, they may be made from various metals or metal alloys, including, but not limited to, stainless steel and nickel-titanium alloy, or from various polymers, such as polyvinyl chloride, polyethylene, polyethylene terephthalate, and polyurethane.

FIGS. 5A, 5B, and 5C show a variation of the described delivery system 500 in which a member of electrolytic delivery joints are used to deploy an implant 502, such as a stent.

The electrolytic delivery joints shown here (e.g., 504 in FIG. 5C) are well known as controllable delivery joints for placement of vaso-occlusive coils. One such commercially available device using an electrolytically detachable joint is sold by Target Therapeutics, a subsidiary of Boston Scientific Corp., as the Guglielmi Detachable Coil (or "GDC"). Numerous patents to Dr. Guglielmi describe the theory of its use.

In essence, the electrolytically erodible joint is a section of an electrical circuit that is not insulated and is of a metallic material that does not form insulating oxides when exposed to an aqueous environment (e.g., aluminum and tantalum) and is sufficiently "non-noble" that is will either electrolytically erode by ionic dissolution into an anatomical fluid or, perhaps, electrochemically erode by forming readily soluble oxides or salts.

The erodible joint 504 shown in FIG. 5C is a bare metal of a size, diameter, etc. that erodes away when a current is applied to insulated wire 506. The current flow is from a power supply through insulated wire 506, bare joint 504, into the ionic anatomical fluid surrounding the site to be treated, and back to a return electrode situated perhaps on the patient's skin and then back to the power supply. The current flows through the circuit so long as the joint 504 exists.

With that background, FIG. 5A shows a device having several joints (504, 508, 510, 512) that each may be independently severed to controllably deploy the implant 502. Implant 502 is shown having coils (514, 516) (FIG. 5B) that are terminated at each end by an erodible joint and that, prior to the severing of a joint, hold this implant 502 to the surface of the delivery member 520. The implant 502 is self-expanding, once released. The wires forming the two coils in this variation slide within the implant or "uncoil" and thereby allow the implant body itself to expand. The coils may comprise (if electrically connected to the erodible joint) a metal that is higher in the Mendelev Electromotive Series than is the composition at the electrolytic joint or the coils may comprise a polymer that may be bio-erodible or not.

In any case, a suitable way to assure that the coils (514, 516) maintain the low profile of the implant 502 during delivery is via the placement of the various conductive wires or elements (506a, 506b, 506c, 506d) through the adjacent holes (524, 526, 528) and fill the holes with e.g., an epoxy to hold all in place. Independently causing current to flow through each of the joints will release the implant in the region of the released joint. Once all joints are eroded, the implant is released.

Although release from proximal and distal ends of the tubular form of the implants has been described, detachment from a delivery guide is not so limited. In another variation, the stent is attached to the delivery guide at one or more positions along the length of the stent, in addition to attachment at the proximal and distal implant ends. Once the distal stent end is released, the additional attachments may be independently released until detachment at the proximal implant end releases the implant entirely from the delivery guide. Serial release may provide better control of positioning in tubular organs.

FIGS. 5D and 5E show in more detail, the components of an electrolytic joint (as may be found in FIGS. 5A, 5B and 5C) and another electrically actuated joint using a meltable or softenable or polymerically sizable joint.

FIG. 5D shows the insulated wire 506a with insulation 523 and conductor 525. The electrolytic joint 504 is also shown. In this variation, the wire 506a is shown to be secured into hole 524 in the delivery guide wall 520 by, e.g., an epoxy 527, an alternative or cooperative band or component 529 holding the wire 506a to the surface of guide member 520 is also shown. After erodable joint 504 is eroded, the implant of 502 expands and leaves the securement band 529 on the delivery guide 520.

FIG. 5E shows a similar variation but the joint comprises a thermoplastic adhesive or shape changing polymer 531 situated on the end of wire 525 and within a cup or other receptacle 533. The adhesive is of the type that changes form or viscosity upon application of current to the joint. In this variation, the thermoplastic is rendered conductive, but resistive, by introduction of material such as carbon black into the polymeric adhesive. As soon as the polymer changes its shape, form, or phase, the implant expands to the desired form about the central guide member 520 again, the wire may be held in place with an adhesive 527 if so desired.

Although the figures show wires and other remnants of the joints remaining exterior to the central guide member 520 and the others shown and described here, it is desirable that these not be situated in such a way that they will harm the tissues into which they are placed.

Delivery Method

The implant delivery devices described herewith may include multiple implants on a single delivery guide or may be used in conjunction with other instruments, as seen appropriate, to treat the target site. In general, the tubular organ of interest is percutaneously accessed, but the method of accessing will usually be dependent on the anatomy of the organ, medical condition being treated, health status of the subject, and the like. Consequently, access by a laparoscopic or open procedure may also be obtained.

Figure 6A:
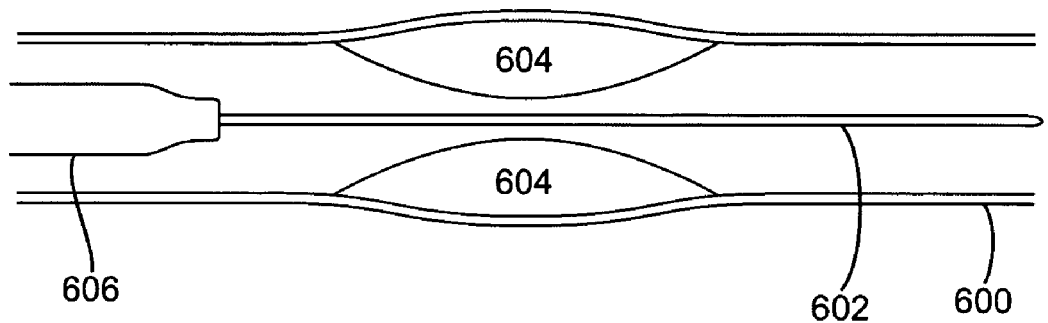
Figure 6B:
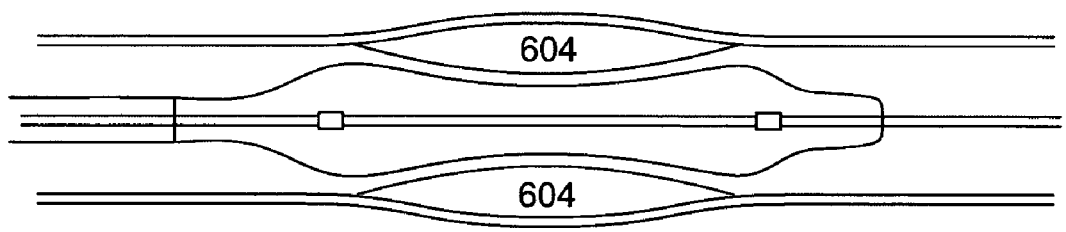
Figure 6C:
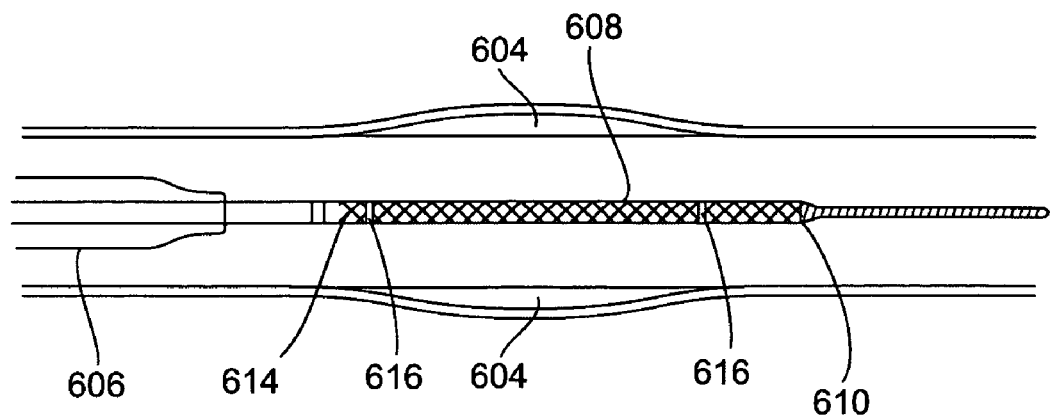
Figure 6D:
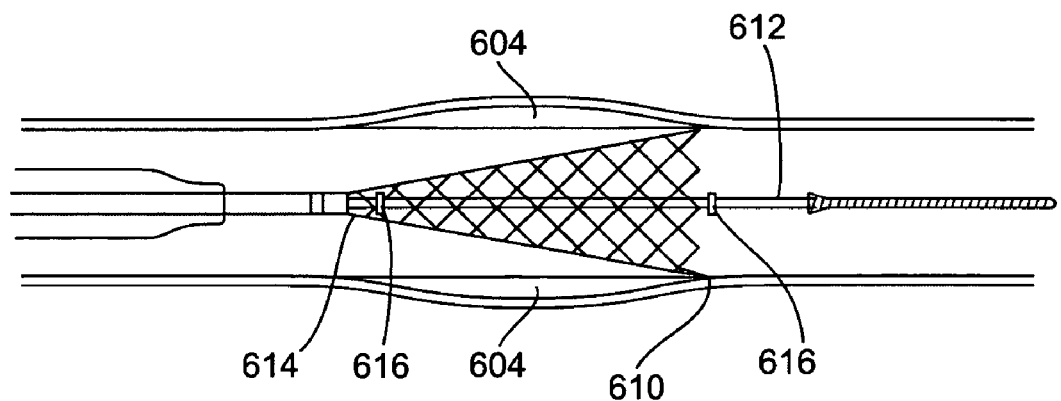

FIGS. 6A-6D show the general method of deploying a stent using my described system. After obtaining access to the tubular organ of interest 600 (blood vessel in FIG. 6A), a delivery guide 602 is placed through the selected area of stenosis 604 at the target site. A balloon catheter 606 is then advanced over the delivery guide 602, and balloon angioplasty performed to dilate the area of stenosis 604 (FIG. 6B). The balloon catheter 606 is then retracted proximally and the delivery guide 602 exchanged for a stent delivery device 608 (FIG. 6C). Appropriate placement of the stent is guided by radioopaque markers 616 on the delivery guide 612. The distal end 610 of the stent is then released from the delivery guide 612. At this point, stent position may again be checked by verifying the location of the radioopaque markers. The proximal stent end 614 is then released from the delivery guide 612.

If desired, an embolic filter may be used during stent deployment to filter any debris generated during the procedure. The filter will usually be attached to the delivery guide such that it filters debris distal to the stent, but may also be attached to the delivery guide proximal to the stent, or both distal and proximal to the stent. The filter may be of any design, as long as it does not affect the substantially atraumatic, low profile, and controlled release characteristics of the stent delivery device. Typically, the filter is basket-shaped, and made from a shape-memory material, e.g., an alloy of titanium and nickel. The filter will usually be contained within the balloon catheter lumen, and deployed to its predesigned shape once the balloon catheter is removed. Following placement of the stent, the balloon catheter may be advanced over the delivery guide to enclose the filter with any accumulated debris. The balloon catheter, filter, and delivery guide may then be removed from the body.

Applications

The implant delivery system may be used in mammalian subjects, preferably humans. Mammals include, but are not limited to, primates, farm animals, sport animals, cats, dogs, rabbits, mice, and rats.

The system may be employed for implant delivery into lumens of tubular organs including, but not limited to, blood vessels (including intracranial vessels, large vessels, peripheral vessels, aneurysms, arteriovenous malformations, arteriovenous fistulas), ureters, bile ducts, fallopian tubes, cardiac chambers, ducts such as bile ducts and mammary ducts, large and small airways, and hollow organs, e.g., stomach, intestines, and bladder. The system may also be employed for implant delivery into solid organs or tissues including, but not limited to, skin, muscle, fat, brain, liver, kidneys, spleen, and benign and malignant tumors. Preferably, the implant is delivered to a target site in a blood vessel lumen.

Clinically, the system may generally be used to treat stenosis of various tubular organs, arising from such etiologies as atherosclerosis, autoimmune conditions, scarring, or exterior compression, e.g., as may be seen with a neoplastic process. The system may also be used to treat medical conditions in which luminal occlusion is desired, e.g., to treat aneurysms, arteriovenous fistulas, and arteriovenous malformations. Furthermore, the system may be employed to deliver implants into such areas as joint spaces, spinal discs, and the intraperitoneal or extraperitoneal spaces.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

The invention claimed is:

1. A method of coronary vessel treatment comprising:
    advancing a balloon catheter to a treatment site;
    performing an angioplasty by dilating the balloon catheter at the treatment site to dilate an area of stenosis;
    retracting the balloon catheter proximally away from the treatment site;
    advancing a guidewire-less delivery guide including a self-expanding stent distally to the treatment site, wherein the stent is not sheathed during advancement;
    releasing the stent to self-expand from the guidewire-less delivery guide while a portion of the guidewire-less delivery guide is within a lumen of the balloon catheter.

2. The method of claim 1 wherein the releasing comprises a mechanical detachment process.

3. The method of claim 2, wherein the guidewire-less delivery guide comprises an actuator for releasing releasable retainers and wherein the delivery guide has only a single passageway from its proximal to its distal end, the passageway containing the actuator, and wherein the actuator does not extend beyond the distal end of the delivery guide.

4. The method of claim 1 wherein the releasing comprises a hydraulic detachment process.

5. The method of claim 4, wherein the guidewire-less delivery guide comprises an actuator for releasing releasable retainers and wherein the delivery guide has only a single passageway from its proximal to its distal end, the passageway containing the actuator, and wherein the actuator does not extend beyond the distal end of the delivery guide.

6. The method of claim 1 wherein the releasing comprises an electrolytic detachment process.

7. The method of claim 6, wherein the guidewire-less delivery guide comprises a lumen and at least one releasable joint configured to release upon application of a suitable DC current, and an electrical conductor located at least partially within said delivery guide lumen to supply suitable DC current to and to thereby release the at least one releasable joint.

8. The method of claim 1, wherein the balloon catheter is dilated prior to commencing stent release.

9. The method of claim 1, wherein the guidewire-less delivery guide is advanced solely by manipulation of the delivery guide member from its proximal end.

10. The method of claim 1, wherein the balloon catheter is advanced to the treatment site before the guidewire-less delivery guide is advanced to the treatment site.

11. The method of claim 10, performed without the use of a coronary guidewire.

12. The method of claim 1, further comprising:
    advancing a guidewire to the treatment site, the guidewire being advanced to the treatment site before the balloon catheter; and
    exchanging the guidewire for the guidewire-less delivery guide.

13. The method of claim 1, wherein the angioplasty is performed at the treatment site prior to deploying the stent from the delivery guide.

* * * * *